(12) United States Patent
Martin

(10) Patent No.: US 7,393,364 B2
(45) Date of Patent: *Jul. 1, 2008

(54) ELECTRONICALLY CONTROLLED PROSTHETIC SYSTEM

(75) Inventor: James Jay Martin, Norman, OK (US)

(73) Assignee: James J. Martin, Norman, OK (US)

( * ) Notice: Subject to any disclaimer, the term of this patent is extended or adjusted under 35 U.S.C. 154(b) by 129 days.

This patent is subject to a terminal disclaimer.

(21) Appl. No.: 11/343,066

(22) Filed: Jan. 30, 2006

(65) Prior Publication Data

US 2006/0155385 A1 Jul. 13, 2006

Related U.S. Application Data

(63) Continuation of application No. 10/410,491, filed on Apr. 9, 2003, now Pat. No. 7,029,500.

(60) Provisional application No. 60/371,974, filed on Apr. 12, 2002.

(51) Int. Cl.
*A61F 2/66* (2006.01)

(52) U.S. Cl. .............................. 623/50; 623/47; 623/24

(58) Field of Classification Search .................. 623/24, 623/25, 47–52, 56

See application file for complete search history.

*Primary Examiner*—Bruce Snow
(74) *Attorney, Agent, or Firm*—Gifford Krass Sprinkle Anderson & Citkowski

(57) ABSTRACT

A prosthetic joint system for users comprising a housing having an interior cavity, a center axis in said interior cavity, and an attachment means for fixedly connecting said housing to said user; an inner cylinder disposed in said housing interior cavity wherein said inner cylinder rotates around said center axis of said housing; an appendage attached to said inner cylinder; a sensor system attached to said appendage; and a dampening system, having a power source, in communication with said sensor system, said inner cylinder, and said housing for controlling dampening of the rotation of said inner cylinder around said center axis of said housing.

4 Claims, 16 Drawing Sheets

FIG. 8
FIG. 8A
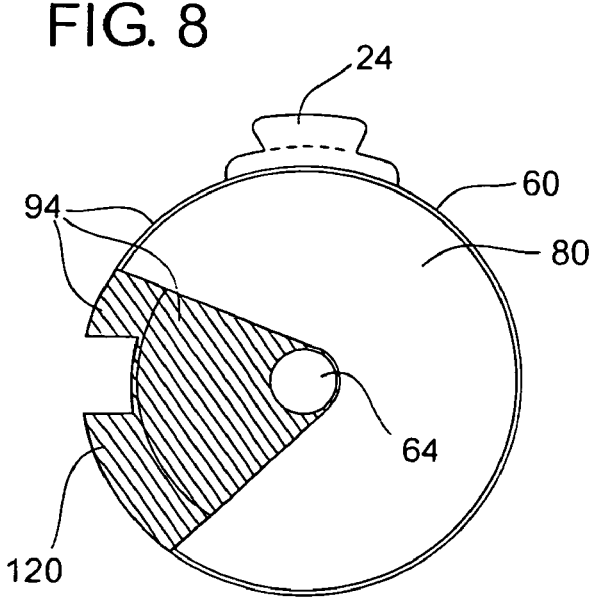
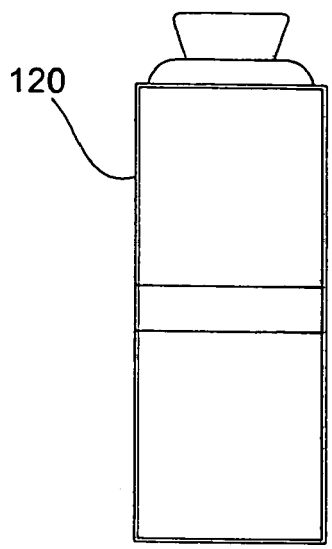
FIG. 9
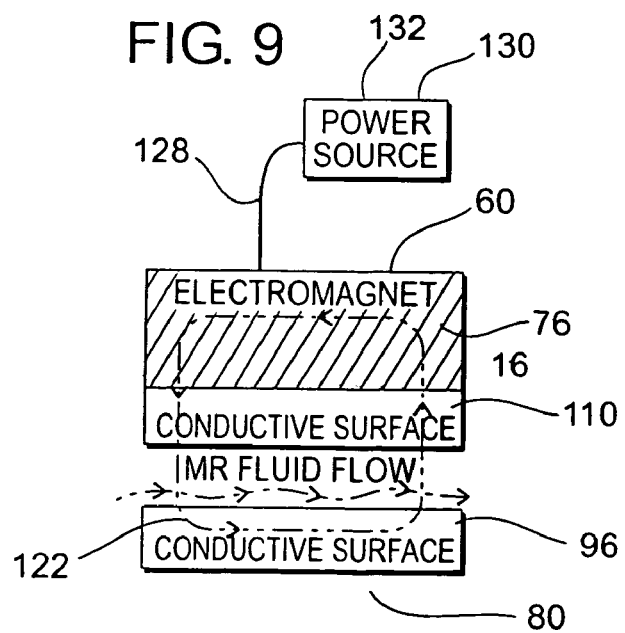
FIG. 9A
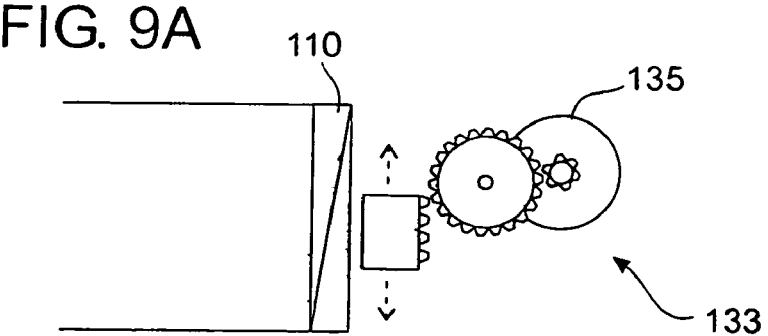

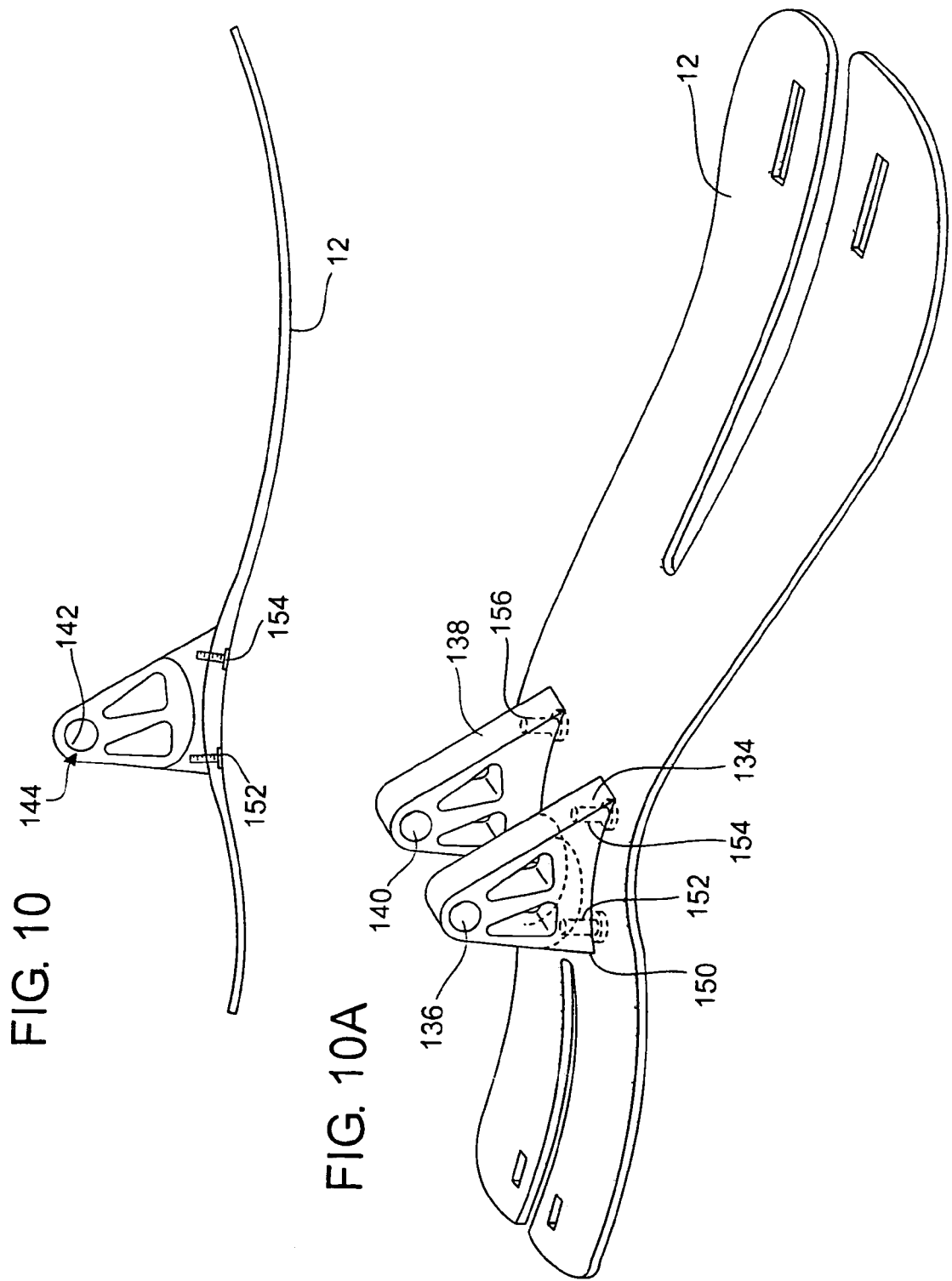

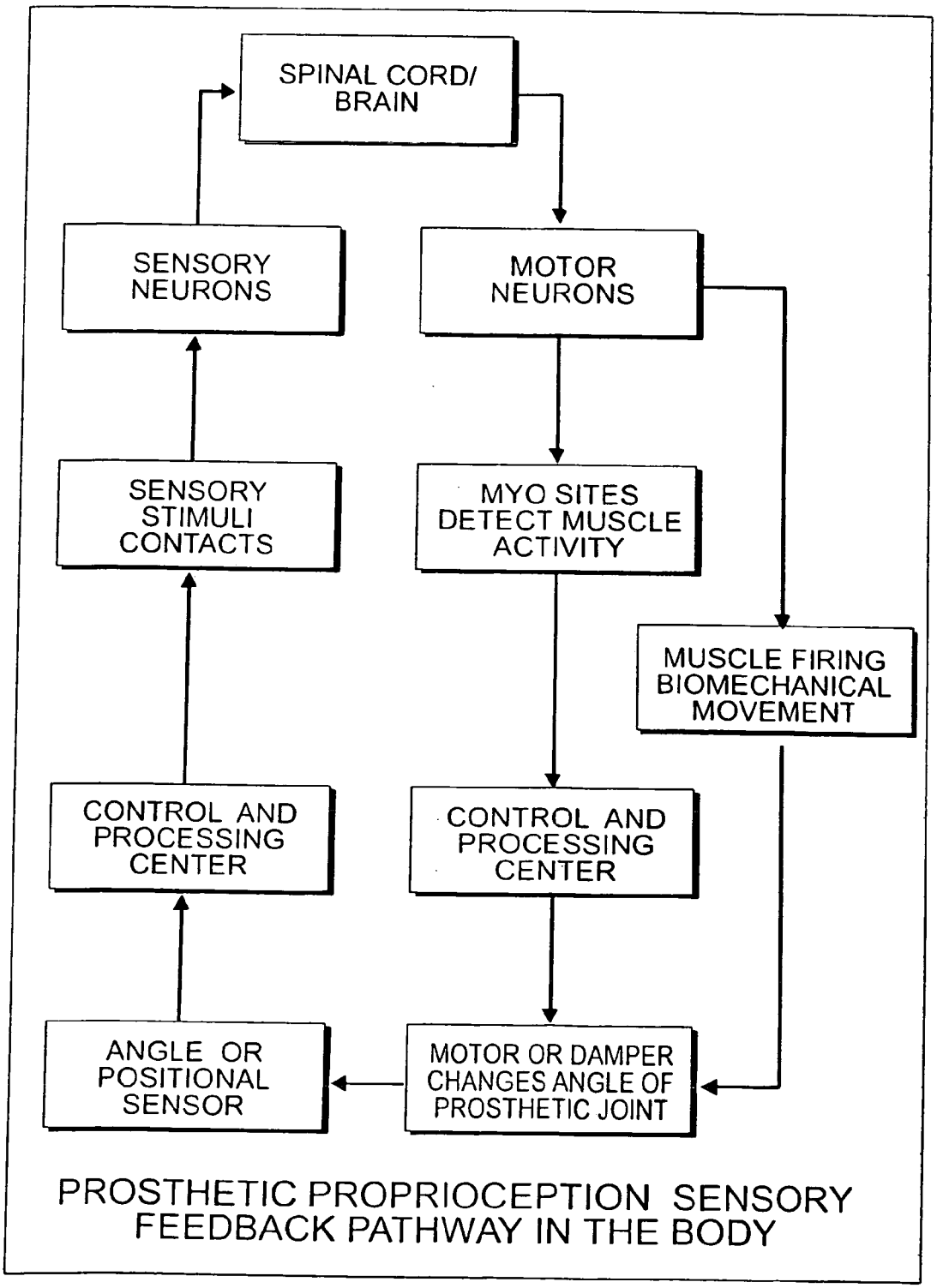

ELECTRONICALLY CONTROLLED PROSTHETIC SYSTEM

CROSS-REFERENCE TO RELATED APPLICATIONS

The present application is a continuation of U.S. Ser. No. 10/410,491, filed on Apr. 9, 2003 now U.S. Pat. No. 7,029,500, in which priority is claimed from provisional patent application U.S. Ser. No. 60/371,974, filed on Apr. 12, 2002. The entire content of the prior applications are hereby expressly incorporated herein by reference.

FIELD OF THE INVENTION

The present invention relates generally to an ankle and foot joint system. More particularly, the present invention is a new and improved prosthetic joint system which simulates natural human locomotion and human biomechanics through sensory feed back, time feedback, electronically controlled dampening joint assembly, and a microprocessor control system.

DESCRIPTION OF THE KNOWN PRIOR ART

As the study of human physiology and anatomy clearly demonstrates, the relative simple action of walking on an even flat surface involves numerous biomechanical complexities. A single step requires constant biofeedback such as continual analysis of proprioception, angulations, timing, and balanced muscular-skeletal functions. In the prior art, the prosthetic industry is continuously attempting to mimic natural human locomotion (NHL), performance and aesthetics.

The field of prosthetics, in general, has made enormous advances in improving amputee and congenitally deformed individuals' performance on multiple levels from general ambulation to competitive sports through improved technology and understanding of human biomechanics. Although, it is known in the art to manufacture ankle and foot prosthetic combinations that have generally increased performance and appearance, the prior art is still deficient on numerous levels as will be discussed in greater detail below.

Many prosthetic feet are optimized for a small or limited range of activities. Typically, models aligned for such activities as daily walking are not optimally aligned for running and vise versa. It is, therefore, desirable to provide a design that allows user to go from walking to running to provide greater user flexibility in multiple activities. Furthermore, while prior art prosthetic devices may have generally moved amputees toward more biomechanically appropriate gait patterns, current mechanically designed prosthetic feet do not allow for significant alterations in gait speed without losing optimal biomechanical characteristics essential with walking or running. Still furthermore, it is desirable to provide a design that allows transition from flat ground to moving up hill or from flat ground to moving downhill with ease, safety, function, and generally traversing uneven surfaces, where the prior art is lacking. There are models in the prior art such as sold under the trademark FLEX-FOOT that may provide greater energy return than other models and models that provide greater uneven ground accommodation such as sold under the trademark COLLEGE PARK. Unfortunately, neither provides both optimal energy return and uneven ground accommodation sufficiently to meet user needs.

It is now contemplated that optimal biomechanical and natural human locomotion functions cannot come solely through a relative simple mechanical device such as found in much of the existing prior art. By example in non-ankle and foot prosthetics, it has been observed in a microprocessor controlled C leg knee design by the company OTTO BOCK that amputees are able to have better gait symmetry, decreased energy expenditure, and a much greater sense of mental confidence in ambulating than non-microprocessor prosthetic knees. It is now contemplated that similar benefits could be observed through this type of design but for a broader spectrum of amputees, including trans-tibial amputees through the use of a computer controlled prosthetic ankle with appropriate sensory feedback mechanisms.

Another consideration lacking in the prior art of ankle and foot devices is the combination of aesthetics and function. A common complaint of many prosthetic foot users is that their prosthetic foot "sticks up" when they sit. This remains a problem due to the prior art prosthetic feet being affixed at a given angle with respect to the prosthesis, thus, during sitting the foot remains pointing upwards as the shin section of the prosthesis has a posterior lean when the amputee is sitting.

Furthermore, the stubbing of a prosthetic foot has proven to be a safety issue for trans-tibial, trans-femoral, and hip-disarticulation amputees alike at all activity levels. The prior art prosthetic feet have attempted to dorsiflex the foot during swing phase in the past, such as with the a prior art design under the trademark or name HYDROCADANCE, but have generally failed to provide the full range of benefits desired, such as being able to be used on a vast array of lower extremity amputees' functional abilities and amputation levels as well as provide optimal energy return characteristics, range of motion, and a life-like appearance, to name a few.

It is desirable to provide a prosthetic foot that also has a much more cosmetic effect through better simulating proper natural human locomotion and allows the foot to plantarflex during sitting to better simulate a real ankle and foot. In this manner, a user's foot and ankle would appear more normal than the tell tale sign of a prosthetic that juts unnaturally up when sitting.

Still furthermore, it is desirable to have a functional prosthetic that may also allow a user to choose from various cosmetically shaped foot shells where the prior art fails. Though prosthetic feet are not commonly seen because they are frequently covered by shoes, cosmetic appearance is a very important aspect to many amputees and other users due to current lifestyle and fashion trends. It is therefore desirable to provide a device that may allow several foot shell templates to choose from much like what is now available with upper extremity prosthetics cosmetic gloves.

What is needed is a prosthetic design utilizing a prosthetic microprocessor, sensory feedback mechanisms for various angle, time, and moment or pressure sensors, and actively providing a means for adjusting plantarflexion and dorsiflexion through prosthetic proprioception which will allow a user to transverse all necessary barriers with appropriate biomechanical precision, stability, and range of activities. Furthermore, it is desirable to provide a design for a very active user who may want to perform daily activities and run, and which provides additional stability and safety for lower activity users who simply need to traverse low level barriers with enhanced safety and stability.

Still furthermore, one of the areas of prosthetics that is very much at its infancy stages is creating prosthetic sensory feedback mechanisms. It is believed that the better the mesh between the human and machine interactions, the more functional, safe, and life-like a user's abilities will become.

Currently found in prosthetic systems used today or in prosthetic research laboratories is the sense of feel system which generally attempts to correspond to human tactile receptors in extremities. The prosthesis detects pressure and stimulates the residual limb in a manner to trick the brain into thinking it is "feeling" with the prosthesis through cerebral projections. In essence the prosthesis attempts to communicate or provide feedback to the user's brain.

Furthermore, there is also myoelectric control which generally attempts interaction from muscular control of extremity muscles. The electrical activity from the muscular actions within the residual limb is picked up by electrodes embedded in, by example, the socket system and cause the prosthetic hand to move in an intended manner. In essence, the brain attempts to communicate or provide feedback to the prosthesis.

Still furthermore, it is understood to attempt a general prosthetic brain wherein correspondence to a sort or proprioception by having the microprocessor embedded in the prosthesis, along with an array of various sensors, cause the prosthetic joint to move in a fashion that matches up to the wearers gait pattern. By example in the prior art, the C-leg system uses a microprocessor or prosthetic brain to constantly analyze how fast it should flex and extend during the swing phase of gait, as well as how much stance stability to maintain during the stance phase of gait, amongst other actions. Such design generally mimics the motion of the sound limb independent of the terrain or slope.

Although prosthetic technology has advanced in recent years, the prior art still has failed to bridge the gap between man made prosthetics and user demand and needs. Likewise, there is also a desire to enhance the body/prosthesis integration through sensory feedback mechanisms and prosthetic proprioception. Therefore, an extensive opportunity for design advancements and innovation remains where the prior art fails or is deficient.

SUMMARY OF THE INVENTION

In general, the present invention is a new and improved prosthetic joint system which provides natural human locomotion and aesthetics where the prior art fails. The present invention generally provides a sensory and time feedback system that works in conjunction with a self-contained microprocessor to control and regulate a dampening system for a joint assembly that utilizes but is not limited to magnetorheological fluid.

Without the intention of limitation, the invention may generally comprise a keel having sensors attached thereto and fixedly attached to an inner cylinder. The inner cylinder is generally disposed in a rotational manner to the outer cylinder or housing which in turn is fixedly attached to a user slower extremity. The inner cylinder rotation is generally controlled by a dampening system that may utilize magnetorheological fluid that receives input from a microprocessor in communication with the sensors attached to the keel.

In this respect, before explaining at least one embodiment of the invention in detail, it is to be understood that the invention is not limited in this application to the details of construction and to the arrangement of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods and systems for carrying out the several purposes of the present invention. It is important, therefore that the claims be regarded as including such equivalent constructions insofar as they do not depart from the spirit and scope of the present invention.

Accordingly, titles, headings, chapters name, classifications and overall segmentation of the application in general should not be construed as limiting. Such are provided for overall readability and not necessarily as literally defining text or material associated therewith.

Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved prosthetic joint system, and more particularly, a prosthetic ankle and foot system that provides greater ease, safety, and function to a wide range of activities such as but not limited to moving from a walk to a run, transverse from flat ground to an up hill grade, or transverse from flat ground to a down hill grade.

It is a further object of the present invention to provide a new and improved prosthetic joint system which is a relatively simple design with few moving parts and thus may be easily and efficiently manufactured.

An even further object of the present invention is to provide a new and improved prosthetic joint system which is of a more durable and reliable construction than that of the existing known art.

Still another object to the present invention to provide a new and improved prosthetic joint system which is susceptible of a low cost of manufacture with regard to both materials and labor, which accordingly is then susceptible of low prices of sale to the consuming public, thereby making such economically available to those in need of such prosthetic devices.

Another object of the present invention is to provide a new and improved prosthetic joint system which provides some of the advantages of the prior art, while simultaneously overcoming some of the disadvantages normally associated therewith.

Yet another object of the present invention to provide a new and improved prosthetic joint system, and more particularly a prosthetic ankle and foot system that is well suited for most K2-K4 amputees as benefit transtibial, transfemoral, hip disarticulation amputees and, generally, all levels of lower extremity amputees.

Still yet another object of the present invention is to provide a new and improved prosthetic ankle and foot system that generally utilizes a keel design wherein energy return is optimized and uneven ground is more easily transversed.

A further object of the present invention is to provide a new and improved prosthetic ankle and foot system for multiple levels of amputation and addresses issues of gait for all activity levels by allowing the foot to dorsiflex through swing phase of gait thus greatly enhancing safety, decreasing mental anxiety, and increasing gait symmetry.

Still another object of the present invention is to provide a new and improved prosthetic ankle and foot system that provides cosmetic effect through better simulating proper natural human locomotion, allowing the foot to plantar flex during sitting, and features a more cosmetically shaped foot shell which may selectively be chosen from a variety of styles.

Another object of the present invention is to provide a new and improved dampening mechanism for artificial joints comprising MR fluid or other fluidly characterized system. The mechanism may be utilized on other prosthetic or orthotic joint systems. Furthermore, the mechanism may allow for retrofitting to prior art, readily available prosthetic feet and ankle joints.

An even further object of the present invention is to provide a new and improved prosthetic joint system which may provide instantaneous communication from the prosthesis to the user wherein feedback is provided such that a sense of spatial and angular orientation of the prosthetic joint is achieved.

Still further, an object of the present invention is to provide a new and improved prosthetic joint system wherein instantaneous communication from the user to the prosthesis is achieved for better regulating, controlling, or positioning the prosthesis.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference would be had to the accompanying drawings and descriptive matter in which there are illustrated preferred embodiments of the invention.

BRIEF DESCRIPTION OF THE DRAWINGS AND PICTORIAL ILLUSTRATIONS

FIG. 3A is a top view of a preferred general construction of a keel and a bracket assembly in accordance with the present invention also showing the intersection of the weight line.

FIG. 8 is a partial cross-sectional side view of a preferred general construction of a joint assembly in accordance with the present invention and also generally depicting the MR fluid.

FIG. 8A is another partial cross-sectional side view of a preferred general construction of a joint assembly in accordance with the present invention.

FIG. 9 is a partial cross-sectional top view of a preferred general construction of a joint assembly conductive circuit in accordance with the present invention.

FIG. 10 is a side view of a preferred general construction of a keel and bracket assembly in accordance with the present invention.

FIG. 10A is a perspective view of a preferred general construction of a keel and bracket assembly in accordance with the present invention.

Figure 11:
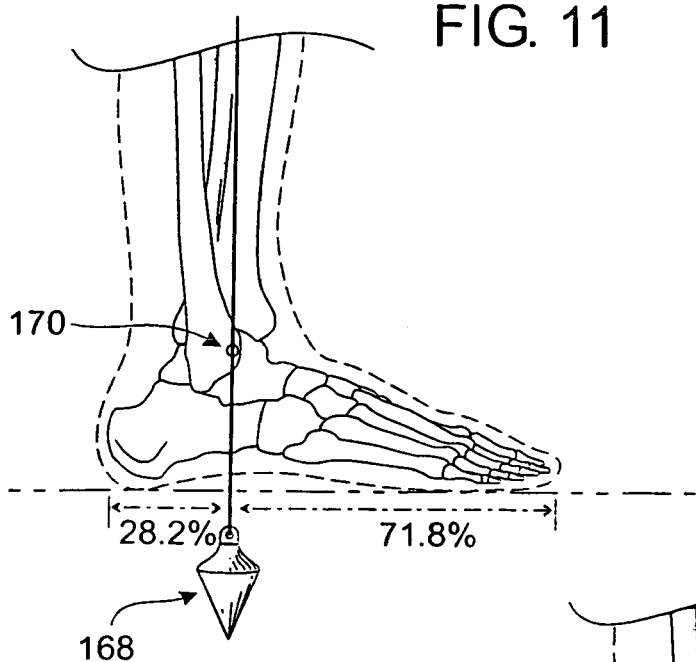
FIG. 11 is general side view of a natural human foot also generally depicting the natural weight line and rotation axis of an anatomical ankle.
Figure 11A:
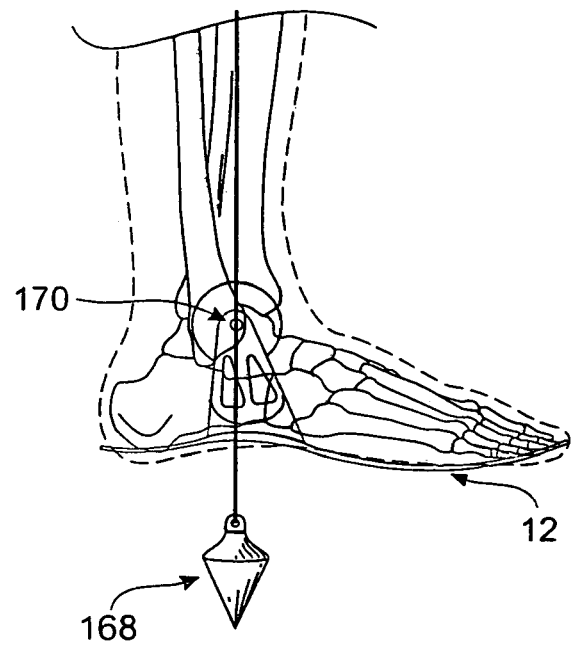

FIG. 11A is general side view of a natural human foot generally depicting the natural weight line, rotation axis of an ankle, and a preferred placement of a keel with MR dampening system center of rotation generally matching up to anatomical center of rotation as well as keel design mimicking the anatomical skeletal plantar surface of the foot in accordance with a preferred construction of the invention.

Figure 11B:
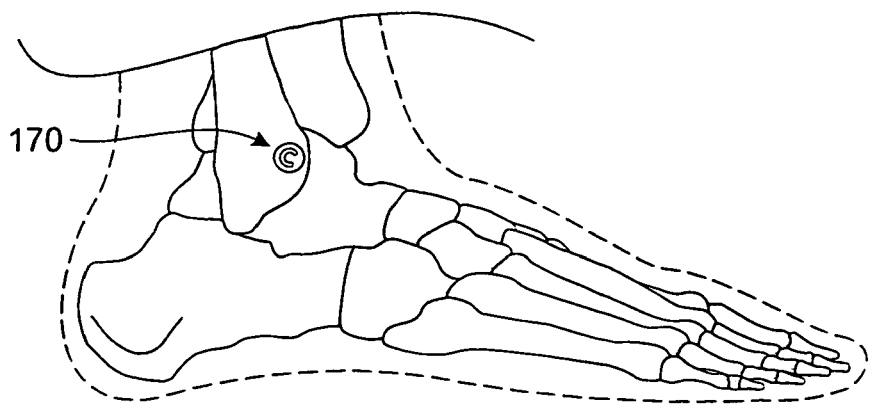

FIG. 11B is general side view of a natural human foot generally depicting the rotation axis or point of a human ankle.

Figure 12:
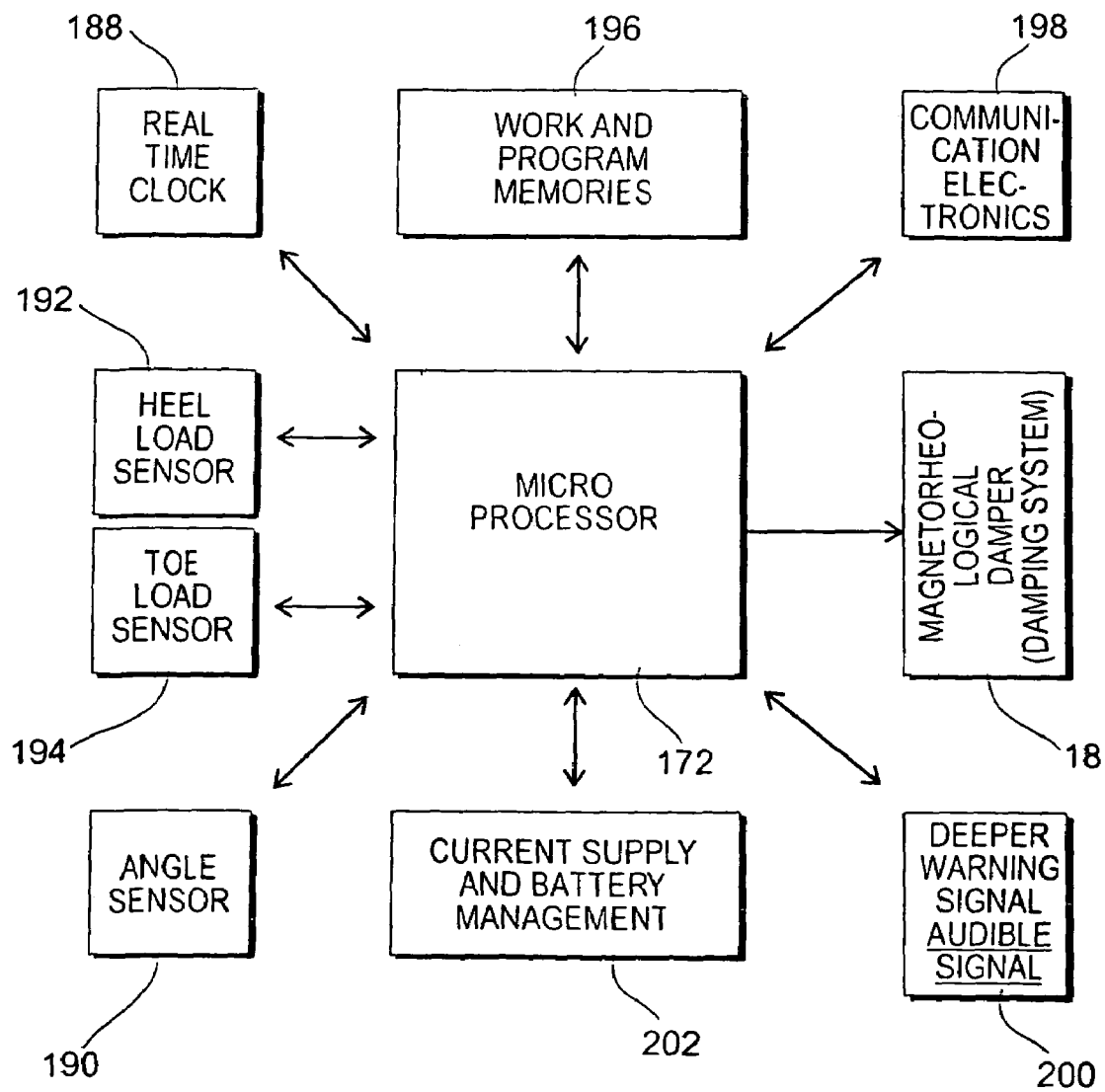

FIG. 12 is a general illustration of a flow chart depicting elements of control electronics in a preferred construction of the invention.

Figure 12A:
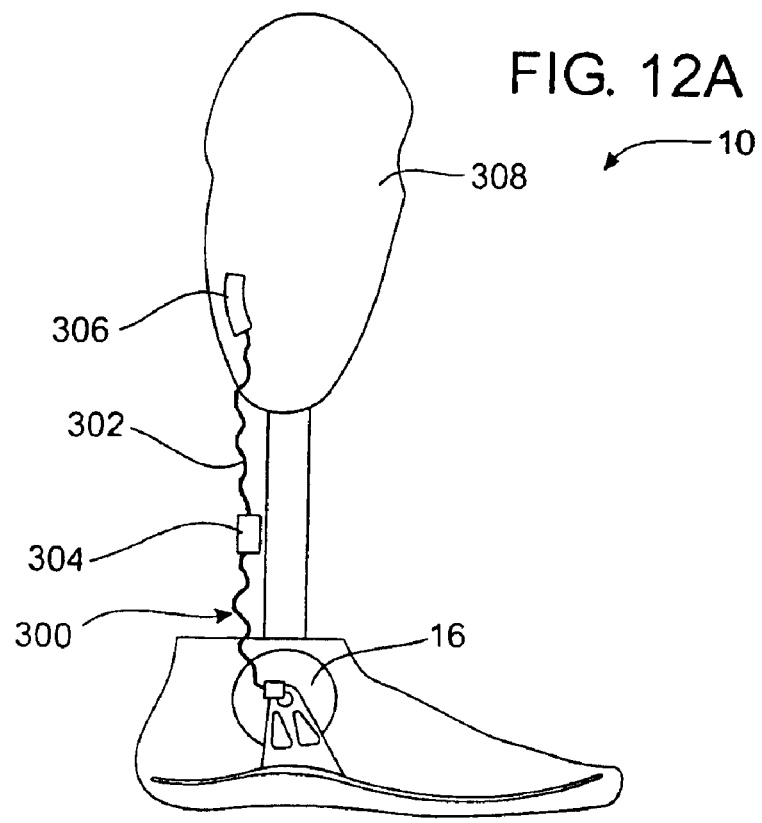

FIG. 12A is a sketch or schematic representation generally depicting a preferred embodiment of the invention wherein sensory feedback is supplied from the invention to a user.

Figure 12B:
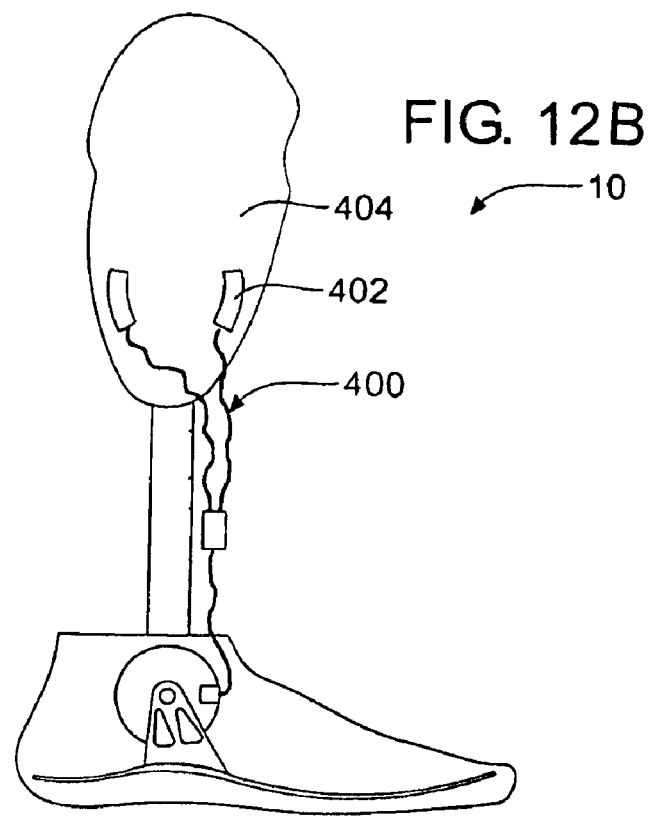

FIG. 12B is a sketch or schematic representation generally depicting a preferred embodiment of the invention wherein sensory feedback is supplied from the user to the invention.

Figure 12C:
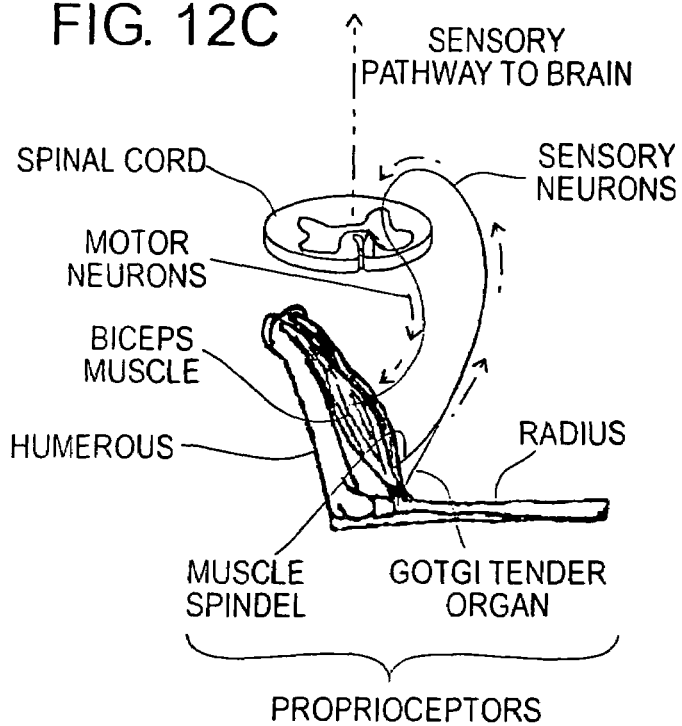

FIG. 12C is a general illustration depicting elements of a natural human system for proprioception feedback pathway.

Figure 12D:
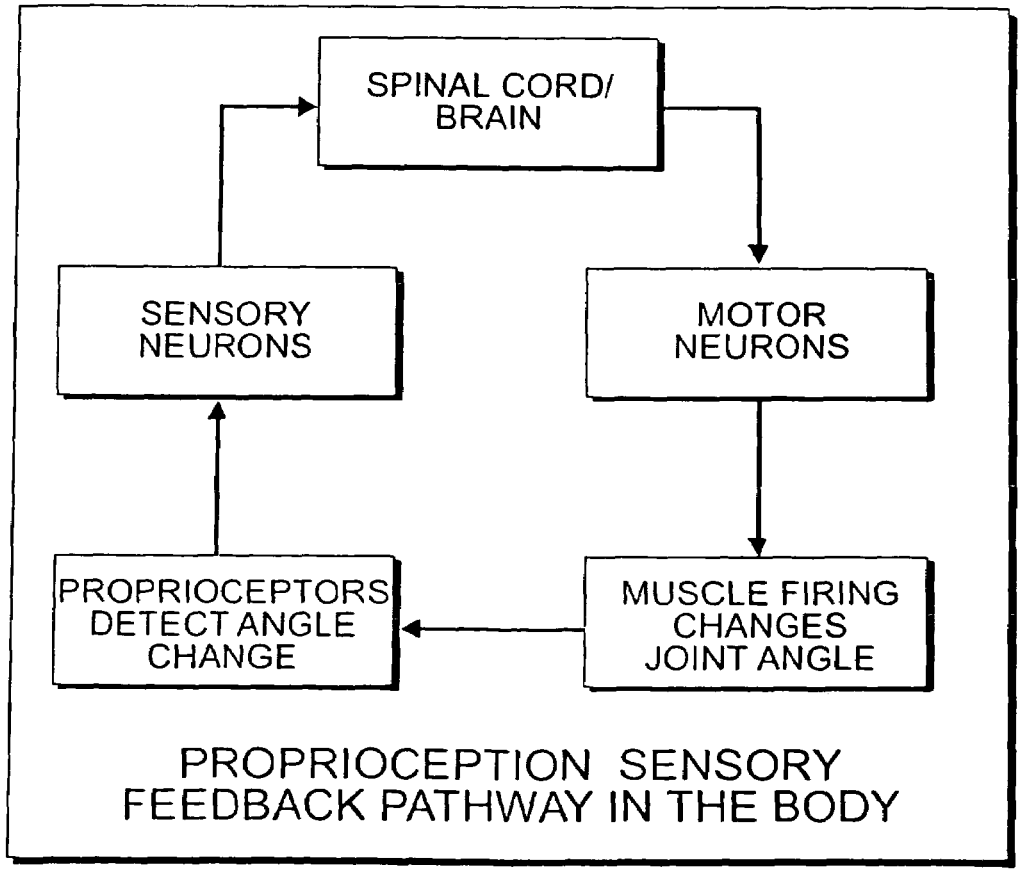

FIG. 12D is a general illustration of a flow chart depicting elements of a natural human system for proprioception feedback pathway.

FIG. 12E is a general illustration of a flow chart depicting elements of a system for proprioception feedback pursuant to a preferred embodiment of the invention.

Figure 12F:
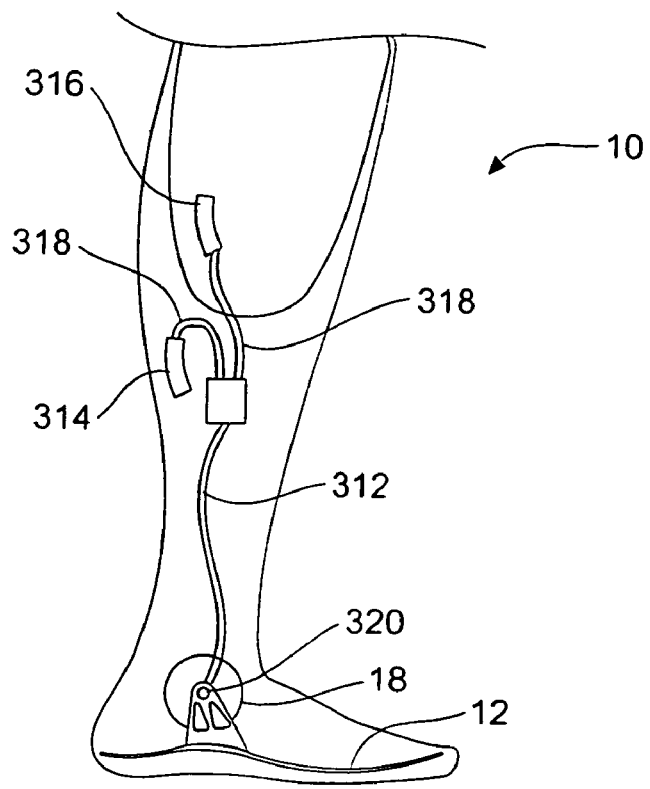

FIG. 12F is a sketch or schematic representation generally depicting a preferred embodiment of the invention wherein sensory feedback is supplied from the invention to a user.

Figure 12G:
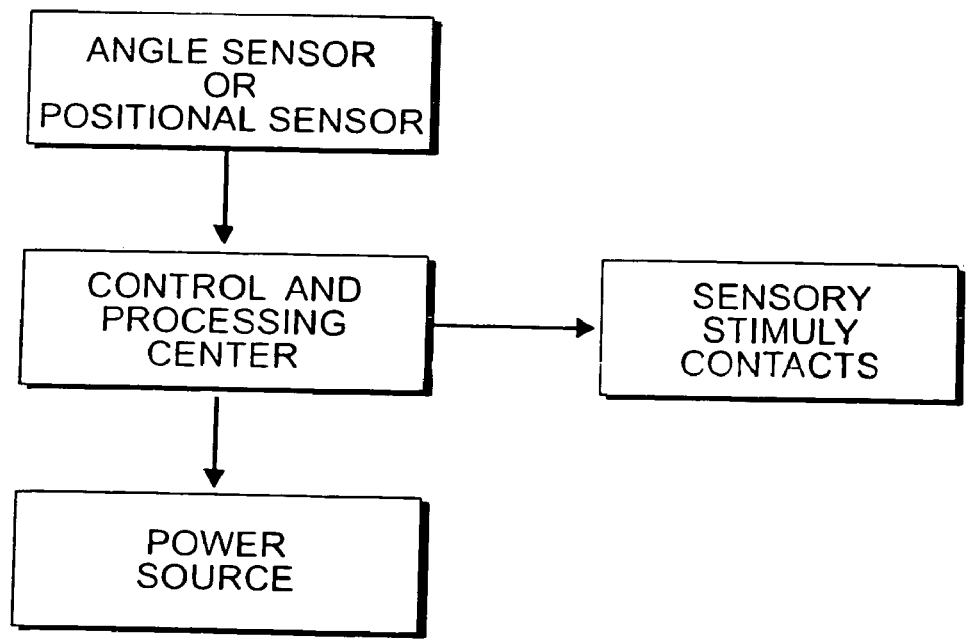

FIG. 12G is a general illustration of a flow chart depicting elements of a system for proprioception feedback pursuant to a preferred embodiment of the invention.

Figure 12H:
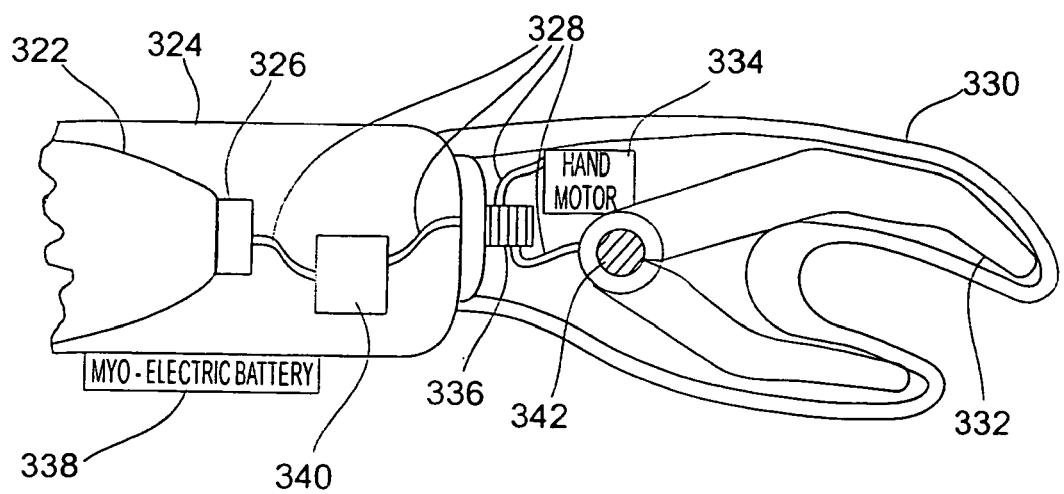

FIG. 12H is a sketch or schematic representation generally depicting a preferred embodiment of the invention wherein sensory feedback is supplied from the invention to a user.

Figure 13:
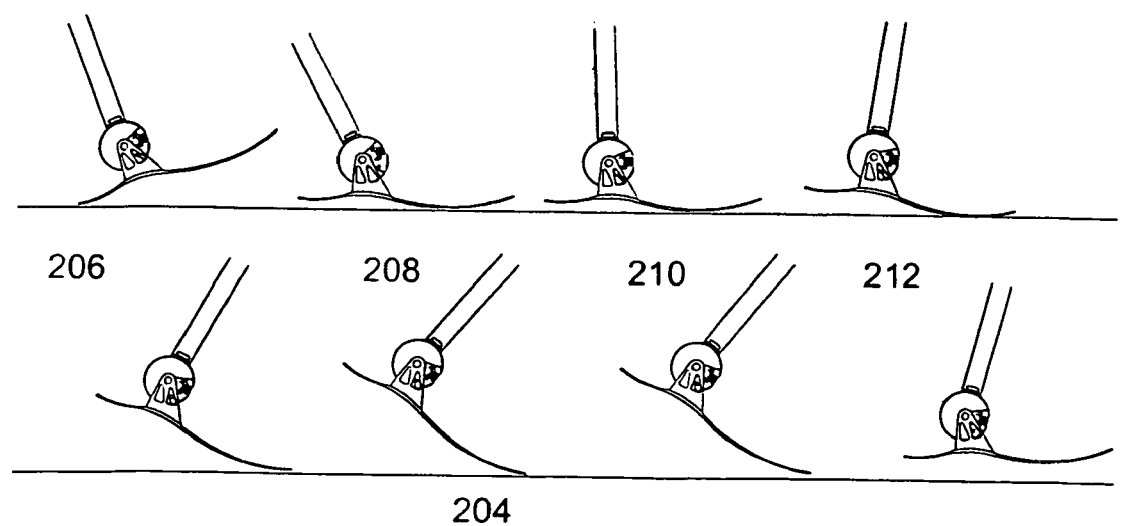

FIG. 13 is a general illustration depicting a preferred construction of the invention throughout gait cycle.

Figure 14:
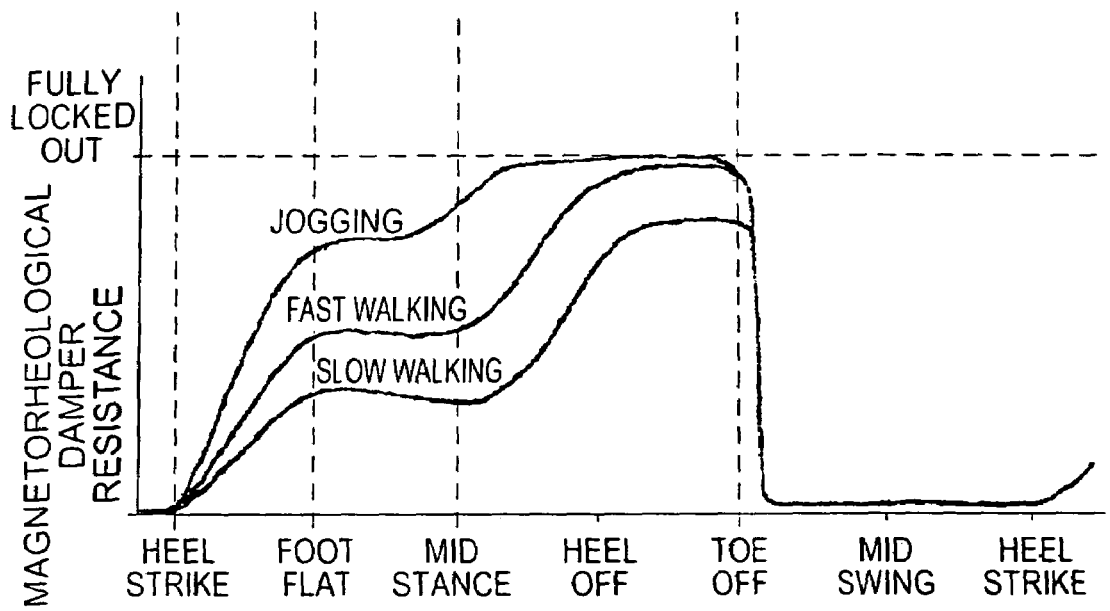

FIG. 14 is a graphical presentation showing general characteristics of magnetorheological fluid damper resistance during a gait cycle in a preferred construction of the invention.

Figure 14A:
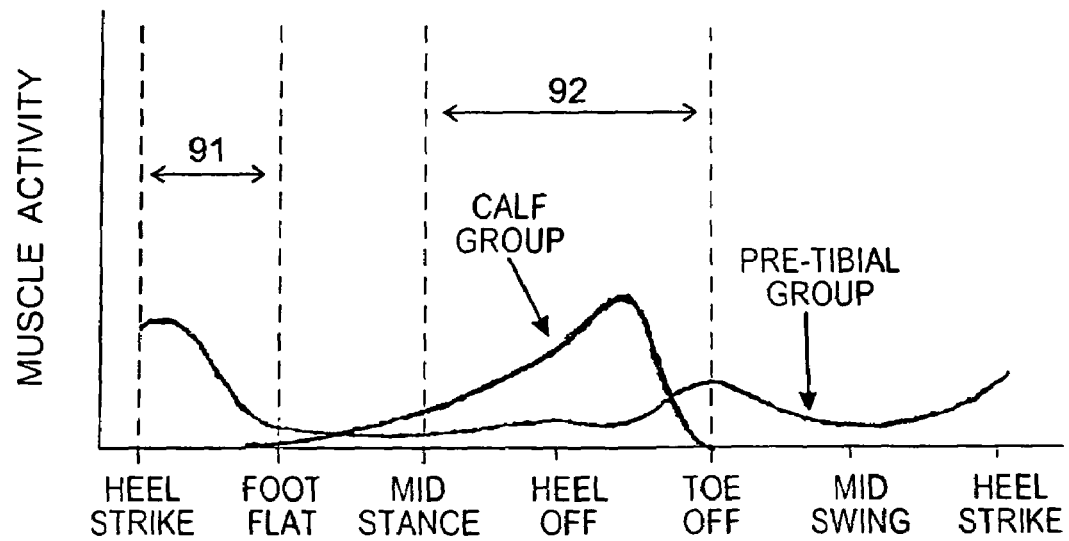

FIG. 14A is a graphical presentation showing general characteristics of natural human muscle activity during a gait cycle.

Figure 14B:
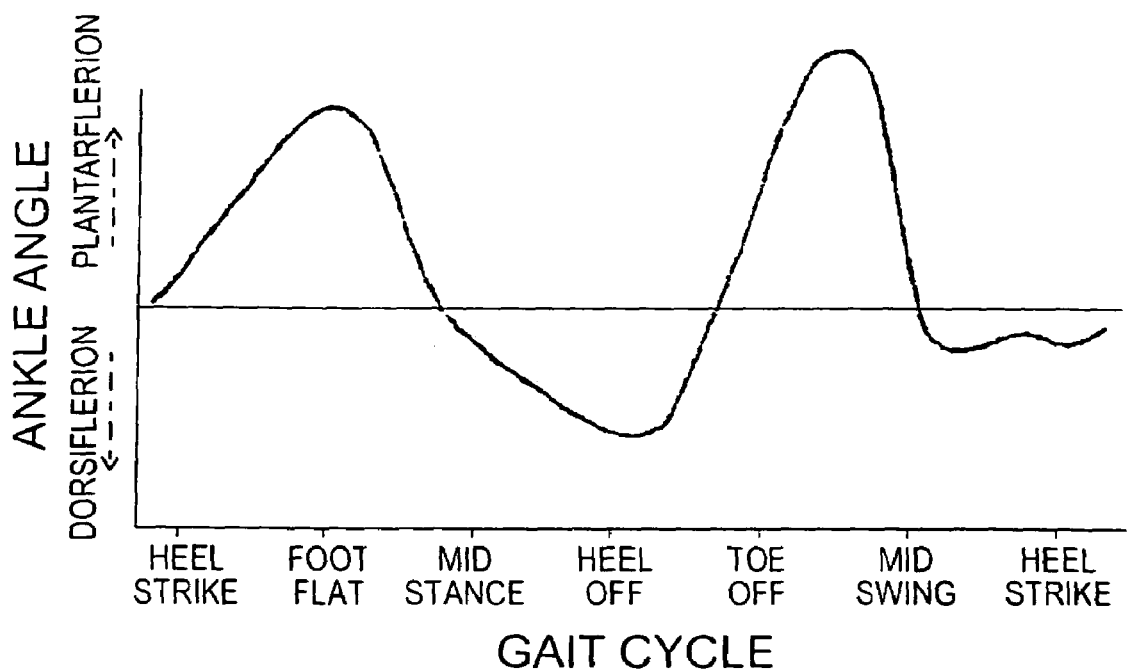

FIG. 14B is a graphical presentation showing general characteristics of natural human muscle ankle angle during a gait cycle.

DETAILED DESCRIPTION OF THE PREFERRED EMBODIMENTS

Figure 1:
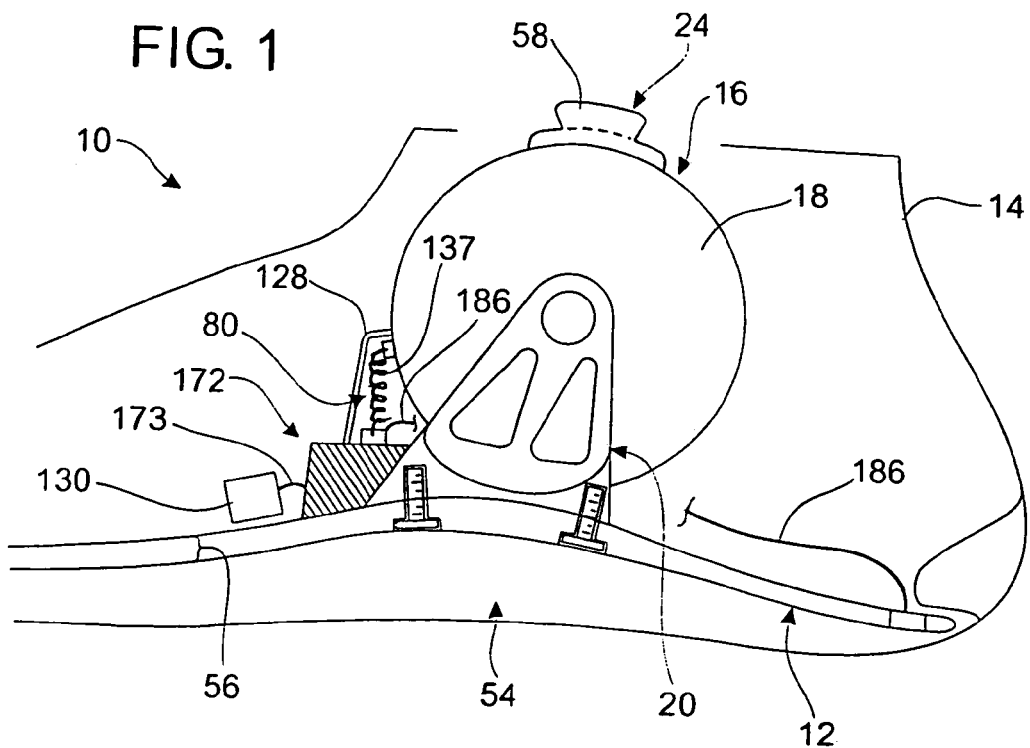
FIG. 1 is a partial cut away side view of a preferred embodiment of the invention.
Figure 2:
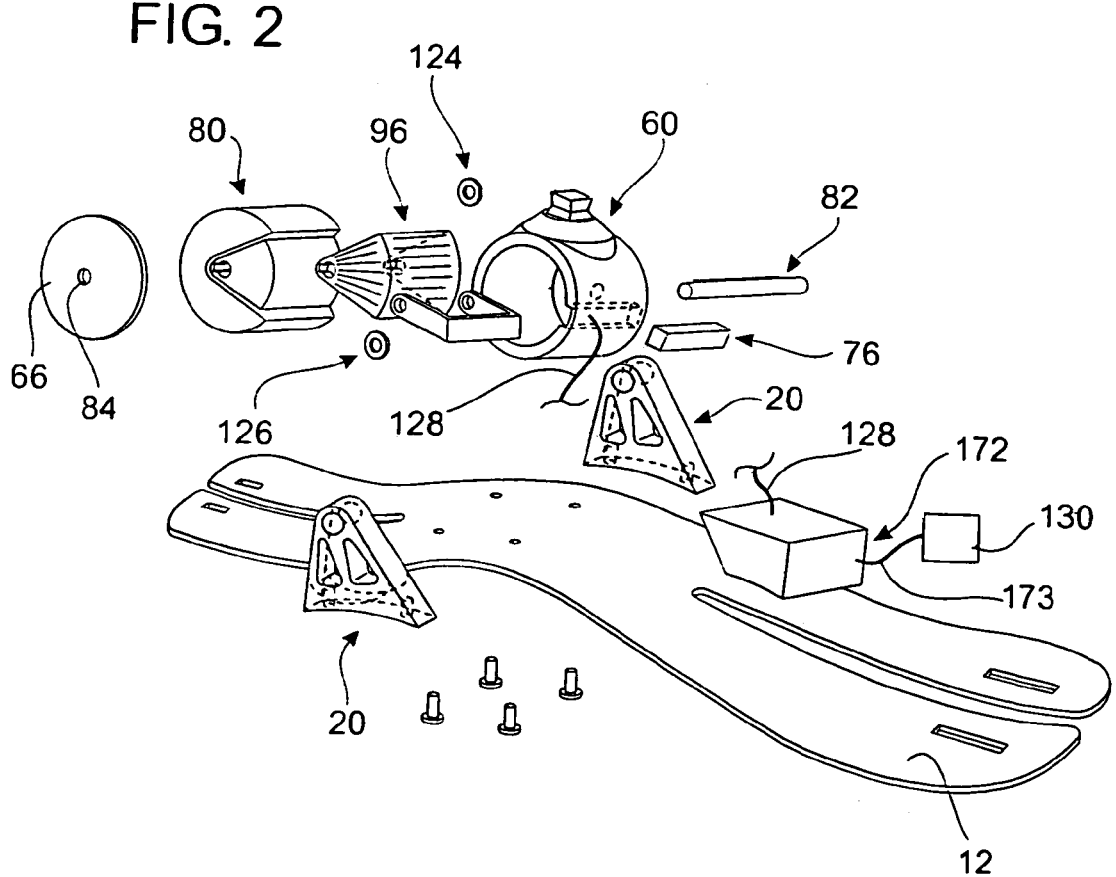
FIG. 2 is a partially exploded perspective view of a preferred general construction in accordance with the present invention.

Referring now to the drawings, wherein like reference numerals designate corresponding structure throughout the views, and referring in particular to FIGS. 1 and 2, reference numeral 10 generally refers to a new and improved prosthetic foot with ankle system, hereinafter referred to as prosthetic foot collectively, in accordance with the present invention. Invention 10 generally comprises keel 12, foot shell 14, ankle joint assembly 16, dampening means or system 18, a bracket assembly 20, sensor system 22, and attachment means 24.

Furthermore, invention 10 is generally shown in a configuration for a right foot. It is understood that a left foot configuration is considered. It is further understood that invention 10 may be used on other joints and associated appendages. The term appendages should not be considered limited to limbs such as arms and legs. Still furthermore, the term joint generally refers to rotationally attached members.

Keel

Figure 3:
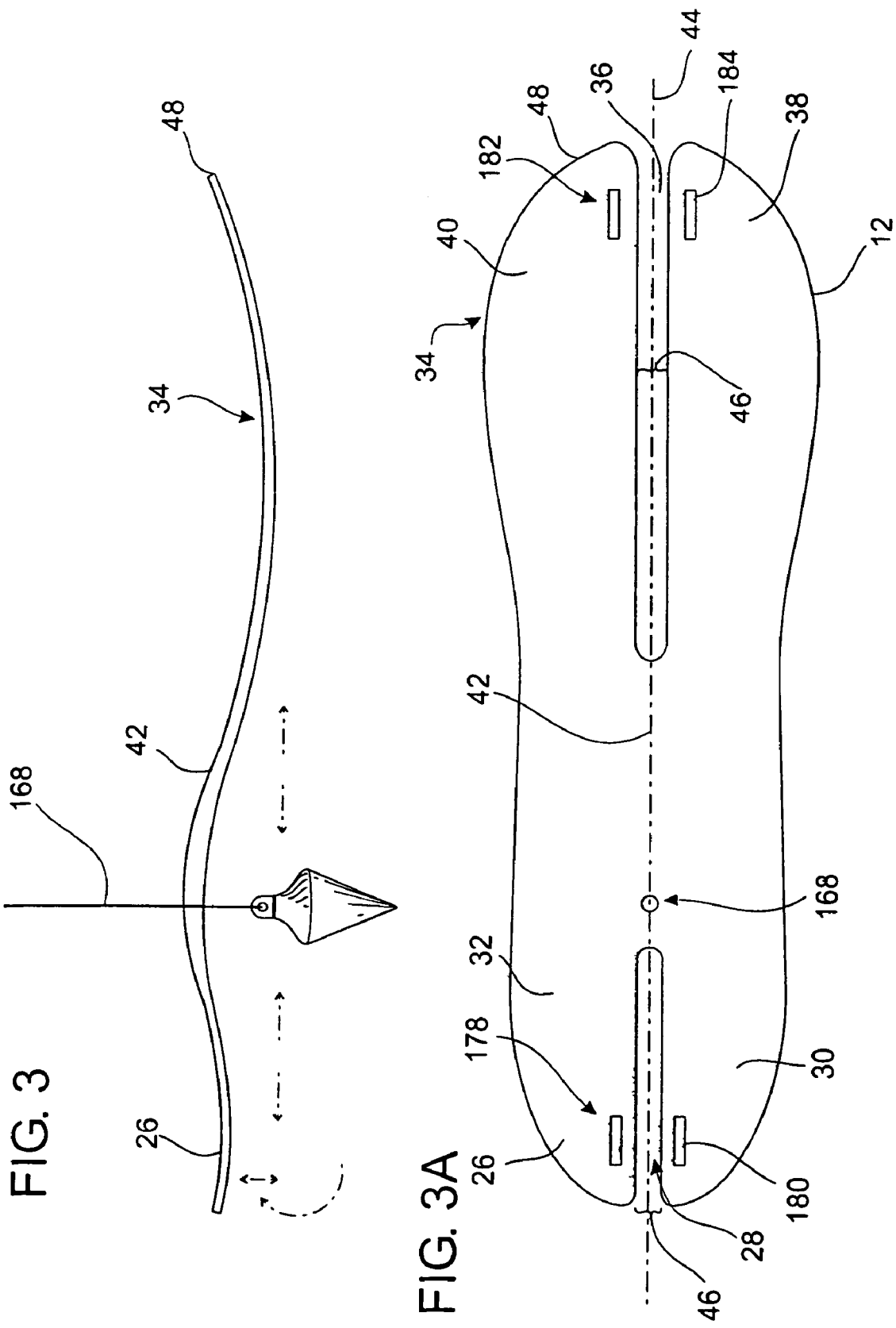
FIG. 3 is a side view of a preferred construction of a keel in accordance with the present invention also generally showing a natural weight line.

Referring to the drawings and in particular FIGS. 3 and 3A, a preferred construction of keel 12 is generally depicted having a heel portion 26 with posterior split 28 that generally separates the heel portion 26 into a medial segment 30 and a lateral segment 32. Furthermore, keel 12 further includes a forefront or toe portion 34 with anterior split 36 that generally separates the toe portion 34 into a medial segment 38 and lateral segment 40. The area generally between heel portion 26 and toe portion 34 is generally referred to as middle portion 42 although it is understood that the term middle should not necessarily be construed as meaning the actual middle point of keel 12.

It is further understood that a keel 12 may include the posterior split 28 and/or anterior split 36 or neither. It is also understood that anterior split 36 and posterior split 28 may run the full length of keel 12 such that keel 12 is generally of a two piece construction (not depicted). Furthermore, both anterior split 36 and posterior split 28 are generally along the midline 44 of keel 12. It is understood that general split construction of keel 12 may generally improve ambulation over uneven ground among other beneficial ambulation.

In a preferred construction, anterior split 36 and posterior split 28 should be of sufficient width 46, respectively, that a reasonable torque on keel 12 should reduce or prevent toe portion 34 medial segment 38 and lateral segment 40 and heal portion 26 medial segment 30 and lateral segment 32, respectively, from contacting or rubbing past the respective segments. Such construction may reduce or prevent a "clicking" noise during walking from said contact. It is also understood that rubber pieces (not depicted) may also be included to reduce or prevent clicking and generally located in posterior split 28 and/or anterior split 36.

In a preferred construction, curvature is contemplated at the end 48 of toe portion 34 and/or at end 50 of heel portion 26 such that a natural rollover during ambulation may be created and to provide keel 12 with correct positioning with respect to the ground to optimize energy return characteristics of keel 12. It is still further contemplated that forefoot or toe portion 34 may be slightly wider than the heel portion 26 to provide additional stability for the user during later portions of stance phase of gait.

It is understood that foot shell 14 should be able to accommodate a broader toe portion 34 such that a cosmetic appearance may still be achieved as well as more closely to approximate the shape of a natural human foot. It is understood that other keel 12 shapes may be considered. Considering many shoes have a built in arch support that often causes a prosthetic foot to tilt laterally in a shoe, it is contemplated that arch 52 of keel 12 in the sagittal view will preferably be relatively high as generally depicted in the drawings. In a preferred construction, a high arch 52 will allow an appropriately tailored foot shell 14 also having a relatively high arch 54, to sit flat in shoes with high arches. Additionally, the curvature will provide smooth rollover characteristics and provide the appropriate positioning of keel 12 with respect to the ground for loading keel 12 to provide appropriate biomechanical simulation. Other heights of keel 12 arch 52 and foot shell 14 high arch 54 may be considered.

In a preferred embodiment, keel 12 may be made from but is not limited to carbon fiber and/or carbon fiber laminates. It is understood that other materials may be used that provide light weight, high strength, high energy return spring characteristics, and may generally have relative simplicity of manufacturing. It is understood that carbon fiber usage allows for some energy return. Still furthermore, carbon fiber or other likewise materials may generally reduce the overall weight, which may be important to assist in decreased energy expenditure through limiting the inertial effects on the musculature of the residual leg, such as with the quadriceps during terminal swing phase of the gait cycle for trans-tibial amputees.

It is understood that keel 12 may generally consist of a thickness 56 to allow sufficient bending movement during stance phase of gait (heel strike through toe off) yet will be sufficiently strong or stiff enough to prevent breaking per the user's weight and activity level. It is still further understood that in a preferred embodiment, keel 12 may be altered to accommodate the resistant nature of bending during walking at different speeds, with varied impacts, and for various terrains which will also be discussed in greater detail below.

As will be discussed in greater detail below, a preferred construction of keel 12 allows for more natural and intentional mimicking of NHL and may provide the energy return at the appropriate time during the gait cycle as with NHL, predominantly at or just before toe-off to simulate gastrocnemious contraction.

In a preferred embodiment, middle portion 42 of keel 12 may be thicker to allow additional strength for attachment to ankle joint assembly 16. It is also contemplated that keel 12 may be flexible enough to have sufficient bending of keel 12 to compensate for NHL shock absorption mechanisms which may have been lost due to amputation such as the movement that can be found in the structure of the human foot like the ligamentous and fibrous bands, as well as with the compressibility of the meniscus pad found under the calcaneous. Thus, it is understood that such construction may allow for a potentially smoother gait. Additionally, increased keel 12 flexibility may allow for better uneven ground accommodation and enhanced energy return. The keel 12 thickness and compressibility may also be tailored to the user's weight and activity level to provide optimum characteristics.

In another preferred embodiment, keel 12 may utilize a split toe design wherein the split may be offset toward one side (not depicted) in order to allow a cosmetic foot shell 14 with a separated big toe in order to allow the user to wear sandals. It is understood that keel 12 may not include any split portions and generally remain with a full non-split keel 12. It is further understood that invention 10 may be adapted to utilize, retrofit, or integrate with existing known keels 12 in the prior art.

Still furthermore, it is understood that keel 12 may be integrally formed with foot shell 14. It is further understood that invention 10 may utilize an attachment means (not depicted) wherein invention 10 may be attached to existing keel 12 designs available in the art.

Foot Shell

In a preferred construction, foot shell 14 may be generally anatomically correct and may further include a sufficiently high arch 54. The keel 12 foot would lock into the foot shell 14 by means that are similar to other internal keel prosthetic feet available such as with FLEX-FOOT designs and OHIO WILLOW WOOD PATHFINDER FEET. It is understood that a SPECTRA sock may be used over foot shell 14 to reduce or prevent squeaking noises arising from the keel rubbing against the foot shell 14. The same internal design of this said foot could be used with either a left or right foot shell 14 for simplicity in manufacturing.

In a preferred embodiment, it may be desirable to provide a foot shell 14 that is generally thin as to not limit the motion of the foot design through stiffness. By example, the OTTO BOCK 1C40 foot provides an optimal foot shell that is generally thin and flexible whereas FLEX-FOOT designs are more generally thicker and less flexible. It is contemplated that a thinner foot shell 14 allows for full keel 12 dynamics although the invention 10 should not necessarily be limited to such.

In a preferred construction, keel 12 is removably attached to foot shell 14. It is contemplated that conventional means known in the art may be utilized. In a preferred construction, keel 12 may generally attach to foot shell 14 by having a small protrusion extending out within the inside of the foot shell 14 in which keel 12 snaps in place underneath.

Attachment Means

Invention 10 generally includes attachment means 24 to a user's lower extremity (not depicted). Attachment means 24 may be but is not limited to a male pyramid 58. It is understood that other conventional attachment means 24 known in the art may be used such as but not limited to threaded screws that mateingly engage, removable and non-removable bolts, removable pins, and so forth may be utilized. Furthermore, it is understood that male pyramid 58 may be of a female configuration and so forth.

Ankle Joint Assembly

Referring once again to the drawings and in particular FIGS. 4, 4A, 4B, and 4C, ankle joint or joint assembly 16 generally comprises a housing or outer cylinder 60 that is generally connected to attachment means 24. In a preferred construction, outer cylinder 60 is generally in a fixed position or non-rotational position relative to lower extremity and attachment means 24. Outer cylinder 60 generally includes an interior cavity 62 and a center axis 64. Furthermore, outer cylinder 60 may include first side cover 66, second side cover 68, and a range of rotation restrictor bar 70.

It is further contemplated that range of rotation restrictor bar 70 may include cavity 72 which may generally be located along perimeter 74 of outer cylinder 60 such that electromagnet 76, which will be discussed in greater detail below, may also generally be installed in a relatively fixed position relative to lower extremity and attachment means 24. In a preferred construction, outer cylinder 60 may be generally constructed of non-magnetic non-conductive material as will be described in greater detail below. In a preferred embodiment, electromagnet 76 is generally disposed in cavity 72 which may also be generally disposed in range of rotation restrictor bar 70.

Once again referring to the drawings and in particular FIGS. 5, 5A, 5B, 5C, and 5D, generally disposed in outer cylinder 60 interior cavity 62 is inner cylinder 80. In a preferred construction inner cylinder 80 generally attaches to keel 12 in a fixed or non-rotational manner such as but not limited to bracket assembly 20 which will be discussed in greater detail below. It is understood that inner cylinder 80 generally rotates around outer cylinder 60 center axis 64. In a preferred embodiment, inner cylinder 80 is made from non-magnetic material in total or in part which will also be discussed in greater detail below.

Figure 6:
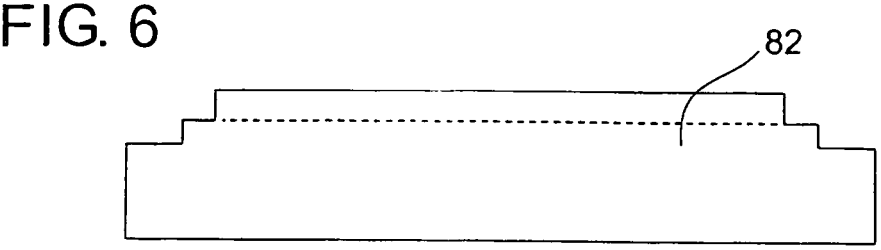
FIG. 6 is a side view of a preferred general construction of a shaft in accordance with the present invention.
Figure 6A:
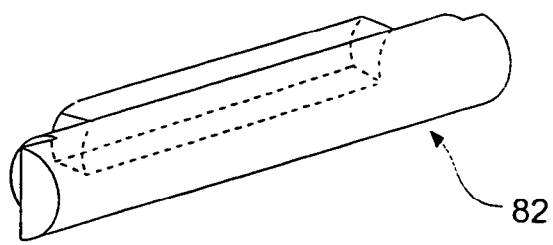
FIG. 6A is a perspective view of a preferred general construction of a shaft in accordance with the present invention.
Figure 6B:
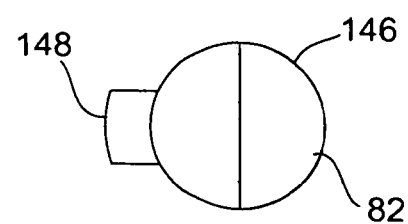
FIG. 6B is another side view or end view of a preferred general construction of a shaft in accordance with the present invention.

Referring to FIGS. 6, 6A, and 6B, in a preferred construction, shaft 82 generally is positioned and aligned along the interior cavity 62 of outer cylinder 60 along center axis 64 whereby inner cylinder 80 is generally attached to shaft 82. Furthermore, shaft 82 generally aligns inner cylinder 80 and outer cylinder 60. Shaft 82 is generally axially aligned and connected by outer cylinder 60 first side cover 66 aperture 84 and second side cover 68 aperture 86. Shaft 82 may be made from non-magnetic material or magnetic material as will also be discussed in greater detail below.

As discussed above, outer cylinder 60 stays in a relatively fixed position relative to lower extremity of user and generally secures shaft 82 such that shaft 82 may rotate along center axis 64. Inner cylinder 80 is generally attached to shaft 82 and rotates relative to user lower extremity. In a preferred embodiment, shaft 82 is in a relatively fixed attachment to inner cylinder 80. It is understood that other conventional rotational means may be provided wherein outer cylinder 60 is in a relatively fixed position relative to user lower extremity and inner cylinder 80 is generally free to rotate respective to user lower extremity.

Inner cylinder 80 is generally constructed such that rotation along center axis 64 is limited. In a preferred embodiment, inner cylinder 80 includes top stop 88 (FIG. 7) which contacts outer cylinder 60 range of rotation restrictor bar 70. Furthermore, inner cylinder 80 may include bottom stop 90 (FIG. 7) which contacts outer cylinder 60 range of rotation restrictor bar 70.

The inner cylinder 80 may be made hollow or with lightweight core to decrease weight. It is understood that inner cylinder 80 may be weighted, filled with a deformable semisolid material, fluid filled, or other such means where the center of gravity (not depicted) of the inner cylinder 80 may move relative to the ankle joint assembly 16.

It is further contemplated that inner cylinder 80 may include a cavity 78 for locating elements of the invention 10 and for possibly providing a water tight compartment for electronics or power source 130 used in association with invention 10 which are discussed in more detail below.

Figure 7:
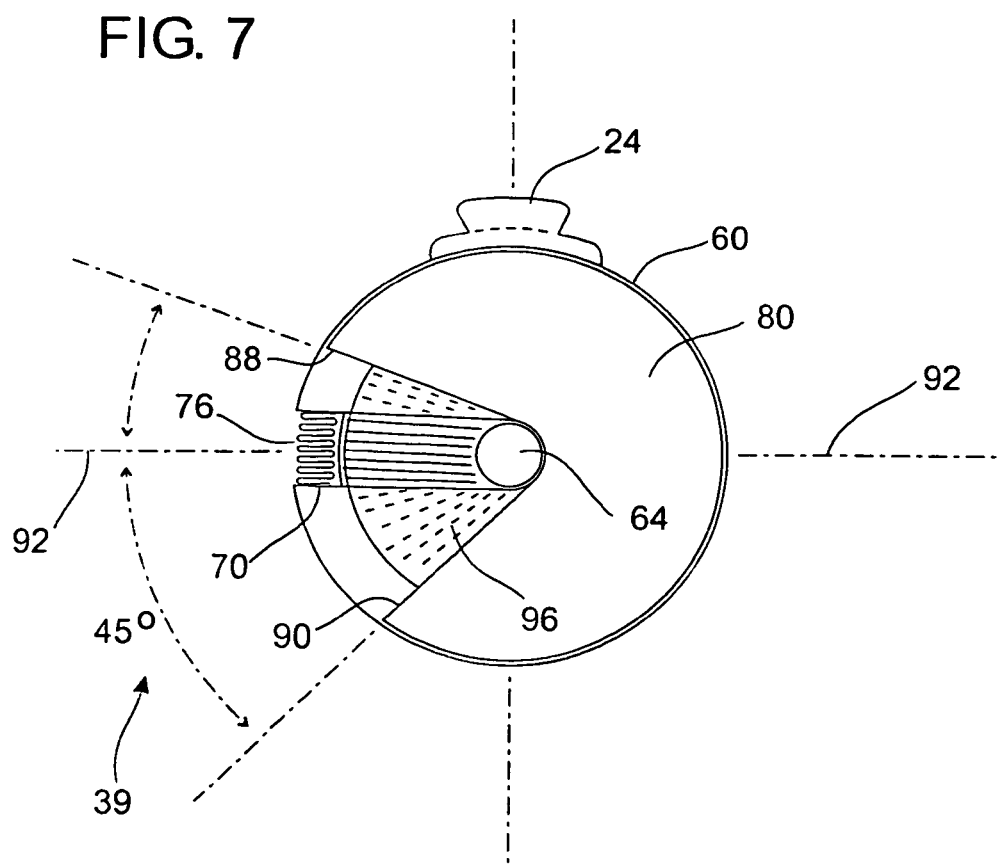
FIG. 7 is a partial cross-sectional side view of a preferred general construction of a joint assembly in accordance with the present invention and also generally depicting the horizontal.

Referring generally to FIG. 7, it is understood that the human ankle has a general range of rotation of about 15 degrees up (from horizontal 92) and a general range of rotation of about 45 degrees down (from horizontal 92). In a preferred embodiment, inner cylinder 80 is generally restricted from rotating up past 15 degrees by top stop 88 contacting outer cylinder 60 range of rotation restrictor bar 70. Furthermore, inner cylinder 80 is generally restricted from rotating down past 45 degrees by bottom stop 90 contacting outer cylinder 60 range of rotation restrictor bar 70. It is understood that the general range of rotation may be increased or decreased and the above example should not be considered limiting. It is contemplated that greater range of motion or rotation may be desired for certain activities requiring more general flexibility and, likewise, more restricted range of motion or rotation for other activities where less flexibility may be desired.

Dampening System

Once again referring to the drawings and in particular FIGS. 8 and 8A, dampening means or system 18, generally refers to a means for controlling keel 12 rotation in association with and respective to the user. Dampening system 18 may generally include electronic control, mechanical function, fluid dynamics, and combinations thereof. It is understood that invention 10 contemplates numerous means such as hydraulic, magnetic, mechanical or other constructions wherein the dampening, general control, or characteristics of the rotation of the joint assembly 16 is achieved.

In a preferred construction, magnetorheological or MR fluid 94 is generally used for dampening the rotation of inner cylinder 80 around the center axis 64 of outer cylinder 60 whereby the MR fluid 94 state of liquidity or viscosity is relatively controlled by selectively charging the MR fluid 94 via use of a permanent magnet or electromagnet 76. By example, where no or little dampening is desired, the MR fluid 94 is not charged and generally stays in a relatively liquid state thereby creating little to no impediment for inner cylinder 80 from relatively freely rotating around center axis 64 of outer cylinder 60. When dampening is desired, the MR fluid 94 is selectively charged to harden or somewhat solidify the MR fluid 94 so that generally a viscous clutch, brake or impediment is created whereby the rotation of inner cylinder 80 around center axis 64 of outer cylinder 60 is slowed and/or halted.

It is also contemplated that MR fluid 94 may further act as a general lubricant for ankle joint assembly 16 outer cylinder 60 and inner cylinder 80. It is still further contemplated that invention 10 may be utilized with hydraulic or other adjustable damper means to control plantarflexion and dorsiflexion. It is understood that the current invention 10 may incorporate other means such as generally fluid type dampening other than MR fluid 94. Likewise it is understood that invention 10 may be carried out with no per se fluid and relay on magnetic and/or mechanical dampening.

In a preferred embodiment, inner cylinder 80 further includes a conductive surface 96 which may integrally be part of inner cylinder 80 or formed in as cover 98. Conductive surface 96 should generally be made from a material that is capable of carrying or conducting an electric or magnetic charge and the term conductive should not necessarily be considered to be limiting. Conductive surface 96 may be made from metal, plastic with metal fibers, or other generally conductive materials or variations thereof. Conductive surface 96 may include a first side 100 and a second side 102 such that a generally larger surface area is contemplated for interaction with MR fluid 94.

Furthermore, conductive surface 96 may be generally near or in communication with shaft 82. Conductive surface 96 may include apertures 104 and 106 for generally attaching with shaft 82. It is contemplated that shaft 82 may be of a conductive, metallic, or the like material whereby MR fluid 94 would also interact with shaft 82 in possible relative conjunction with conductive surface 96. Still furthermore, conductive surface 96 may have serrations 108, ridges or the like.

Figure 4:
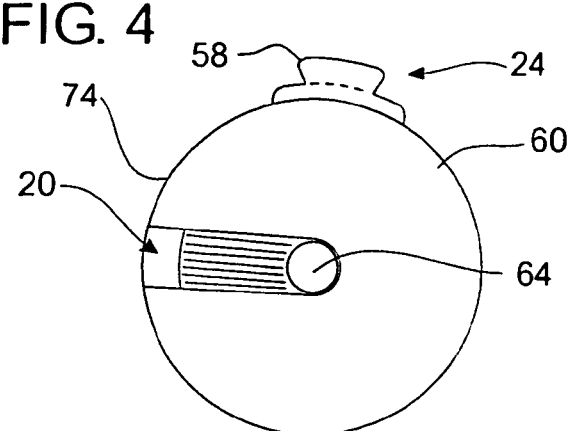
FIG. 4 is a side view of a preferred general construction of a joint assembly in accordance with the present invention.
Figure 4A:
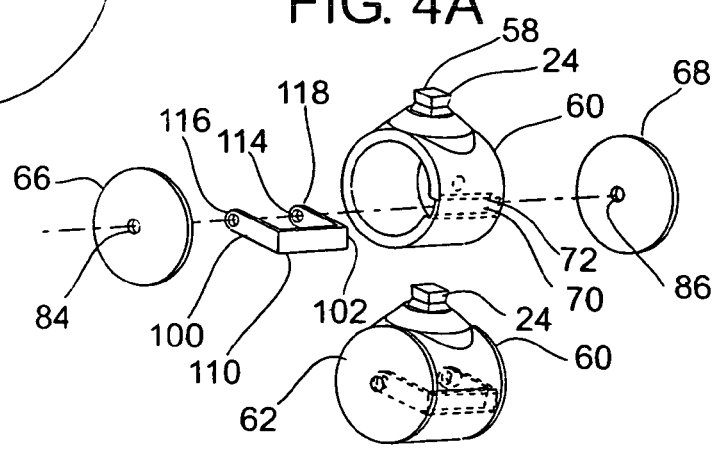
FIG. 4A is a partially exploded perspective view of a preferred general construction of an outer cylinder in accordance with the present invention.
Figure 4B:
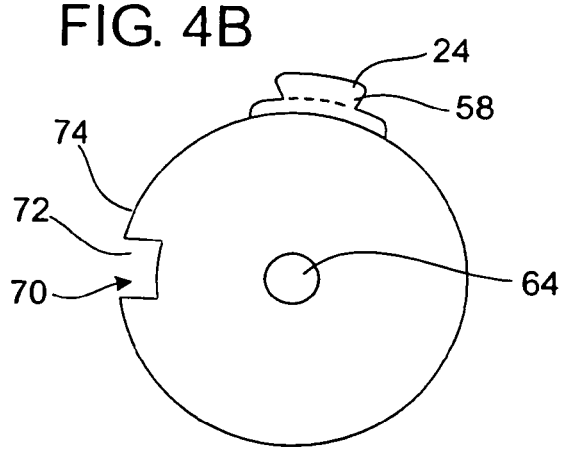
FIG. 4B is a side view of a preferred general construction of an outer cylinder in accordance with the present invention.
Figure 4D:
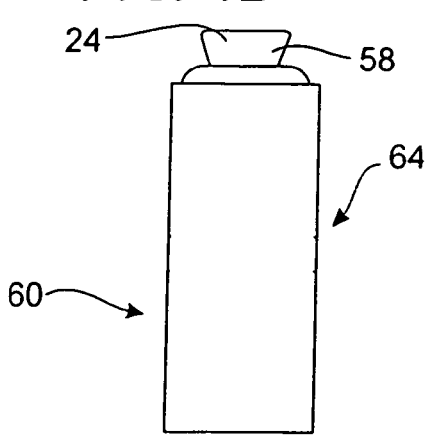
FIG. 4D is another side view of a preferred general construction of an outer cylinder in accordance with the present invention.
Figure 4C:
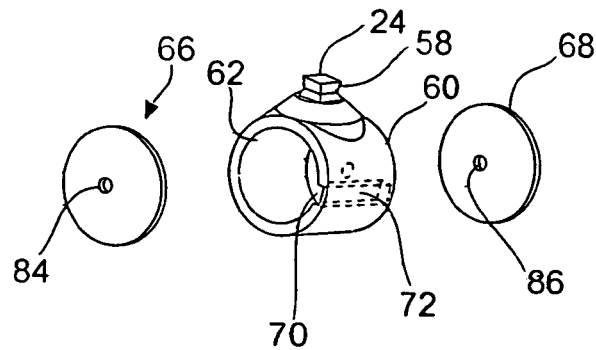
FIG. 4C is a partially exploded perspective view of a preferred general construction of an outer cylinder in accordance with the present invention.
Figure 5:
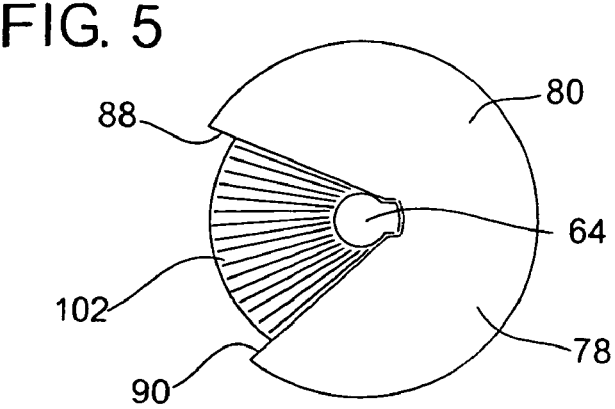
FIG. 5 is a side view of a preferred general construction of an inner cylinder in accordance with the present invention.
Figure 5A:
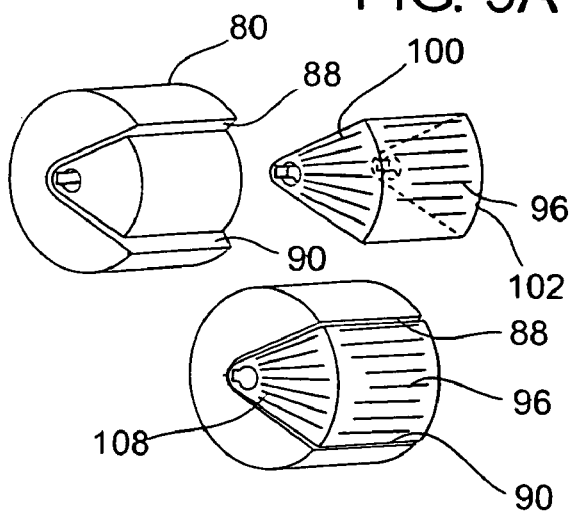
FIG. 5A is a partially exploded perspective view of a preferred general construction of an inner cylinder in accordance with the present invention.
Figure 5B:
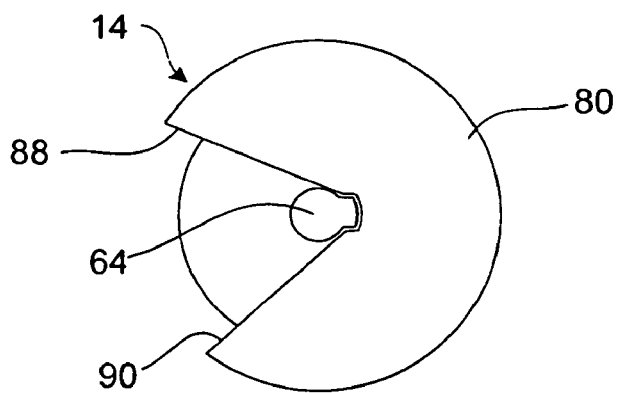
FIG. 5B is a side view of a preferred general construction of an inner cylinder in accordance with the present invention.
Figure 5D:
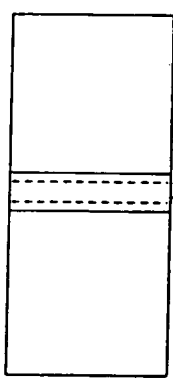
FIG. 5D is another side view of a preferred general construction of an inner cylinder in accordance with the present invention.
Figure 5C:
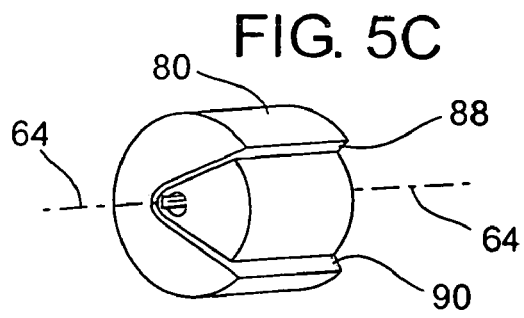
FIG. 5C is a partially exploded perspective view of a preferred general construction of an inner cylinder in accordance with the present invention.

As discussed above, outer cylinder 60 is generally formed from non-magnetic or conductive material. In a preferred construction, outer cylinder 60 includes conductive surface or strip 110 which may be integrally formed with outer cylinder 60 or as separate element 112 as generally depicted. Furthermore, conductive surface or strip 110 have serrations 114, ridges or the like (FIG. 4A). In general, outer cylinder 60 strip 110 is aligned with inner cylinder 80 conductive surface 96. In a preferred construction, strip 110 may further include a first side 117 and a second side 119 which may generally interact with inner cylinder 80 conductive surface 96 first side 100 and second side 102, respectively. Still furthermore, strip 110 may generally connect or be in contact with shaft 82. Conductive strip 110 may include apertures 116 and 118 for generally attaching with shaft 82.

The inner cylinder 80 conductive surface 96 and outer cylinder 60 conductive strip 110 may include serrations 114, ridges or the like in a generally radial direction from center axis 64 in order to increase or help MR fluid 94 lock down in the presence of an electric or magnetic field and thereby increases direct shear mode response. It is further contemplated that such construction would additionally increase the surface area for MR fluid 94 communications and interaction.

It is contemplated that void, space, or cavity 120 is generally created between outer cylinder 60 and inner cylinder 80 and generally filled with MR fluid 94. In a preferred embodiment, inner cylinder 80 is generally disposed in outer cylinder 60 such that a general close proximity may be achieved to limit the amount of MR fluid 94 needed with possible exception to areas specifically where the given distance would be optimized for fluid dynamic characteristics. Furthermore, MR fluid 94 may act as a general lubricant to decrease friction between the inner cylinder 80 and outer cylinder 60 during rotation. It is also contemplated that having the inner cylinder 80 and outer cylinder 60 in a relative close proximity would increase or benefit the structural lateral torque stability of the dampening system 18.

It is still also contemplated that shaft 82 may be made of conductive or magnetic properties in order to assist or decrease or prevent possible leakage of the MR fluid 94. By example, such construction may generally make the MR fluid 94 generally more viscous and not as likely to leak through holes or potential holes in seals.

Now referring to FIG. 9, in a preferred construction, electromagnet 76 is generally in communication or contact with outer cylinder 60 conductive strip 110, which is in communication with or contact with MR fluid 94, which in turn is in communication or contact with conductive surface 96 of inner cylinder 80, thereby forming electric or magnetic flux circuit 122.

Spacers 124 and 126 made from but not limited to nylon may also be utilized in a preferred construction and generally be placed between inner cylinder 80 and conductive strip 110 to decrease or prevent completion of circuit 122 aside from charging the MR fluid 94 in completion of circuit 122.

Power source 130 is generally in contact or communication with electromagnet 76 via wires 128. It is contemplated that the dampening system 18 may have a low draw of energy consumption, and thus a small battery 132 may be utilized. In a preferred construction, battery 132 would preferably be lithium ion in nature but is not limited to such. Power source 130 can be placed anywhere on the prosthesis for ease of replacement and may include an attachment port (not depicted) for recharging. Additionally, for optimizing the weight distribution, power source 130 can be placed externally such as on the socket or pylon. It is also contemplated that the power source 130 could selectively be placed higher, keeping a higher center of gravity for minimalizing inertial forces during running. As discussed above, power source 130 may generally be located in cavity 78 of inner cylinder 80.

Furthermore, electromagnet 76 may also incorporate a safety features to allow a manual lock such as but not limited to a permanent magnet for the event of power loss. It is contemplated that as a potential safety backup, wherein by example a power source 130 level were to decrease to a certain level, a reverse polarity may be created to cause the permanent magnet to slide into position to lock joint assembly 16 or dampening system 18. By example, a permanent magnet may be slid into a desired position to create a positive lock at a fixed angle to allow the user to ambulate with some or all of the motion coming from the keel 12 compression such as may be found in prior art standard prosthetic feet. Once recharging or power source 130 returns to a relative normal condition, the polarity would again reverse back to its normal state, causing the permanent magnet to move out of position, and invention 10 may then operate via the electromagnet 76. As power levels become low, an indicator, such as audible or vibratory alert may be used.

It is further contemplated that joint assembly 16 and dampening system 18 may include a magnetorheological dampening which may operate by both direct shear and pressure driven mode to generally increase the resistance ability of the joint assembly 16. As stated above, dampening system 18 may of numerous construction contemplated within the scope of invention 10.

Referring to the drawings and FIG. 9A in particular, it is still further contemplated that a mechanical based servo/permanent magnet system 133 may be used in conjunction with or as opposed to electromagnet 76. It is further contemplated that tapered magnetic and nonmagnetic pieces which are joined together with which the permanent magnet slides against, via a servo or motor, in order to vary the magnetic field interacting with conductive piece number 110. In a preferred construction, magnet system 133 may include a small servo or motor mechanism 135, such as but not limited to one utilizing gears, to slide back and forth.

Additionally, mechanical based servo/permanent magnet system 133 may include a hydraulic adjustable valve (not depicted) to control the amount of MR fluid 94 passing between outer cylinder 60 and inner cylinder 80. The valve may be controlled as well by a small servo or motor mechanism. It is contemplated that mechanical based servo/permanent magnet system 133 may require less energy consumption and may therefore be beneficial in certain applications. Dampening system 18 may also generally include spring system, dorsiflexion means or dorsiflexion spring system 137. It is contemplated that dorsiflexion spring system 137 may cause the ankle joint assembly 16 to dorsiflex during swing phase of gait. Dorsiflexion spring system 137 may comprise a spring of conventional nature, hydraulic piston, combinations of both or other conventional spring biased devices known in the art. Dorsiflexion spring system 137 may be attached or located anteriorly or posteriorly to the dampening system 18 or ankle joint assembly 16 (compression or extension spring, depending on the location for shortening or lengthening, respectively).

The spring load resistance may be changed through adjusting the spring drive length, changing to a lighter or heavier spring, or adjusting spring placement.

Bracket Assembly

Referring to the drawings and in particular FIGS. 10 and 10A, in a preferred embodiment, bracket assembly 20 would generally comprise a medial bracket 134 having aperture 136 and lateral bracket 138 having aperture 140 wherein aperture 136 and aperture 140 are generally axially aligned and receive shaft 82. Furthermore, medial bracket 134 aperture 136 and lateral bracket 138 aperture 140 may be generally in a circular shape 142 with a flat portion 144 for matingly engaging shaft 82 circular portion 146 and flat portion 148 (FIG. 6B).

In a preferred construction bracket assembly 20 is pivotally connected to outer cylinder 60 such that the rotational movement is along center axis 64. It is understood that other attachment means may be contemplated wherein bracket assembly 20 is connected to inner cylinder 80 in a generally fixed manner and yet in a pivotally rotational manner with outer cylinder 60. It is contemplated that bracket assembly 20 is attached to keel 12 by attachment means 150 such as but not limited to screws 152, 154, 156, and 158. Other conventional attachment means 150 may be used wherein keel 12 may be easily and quickly be removed for other configurations of keel 12.

It is further understood that bracket assembly 20 may be of a single piece construction (not depicted) wherein medial bracket 134 and lateral bracket 138 are joined in the middle on the distal aspect to possibly provide additional stability. The contouring of the brackets assembly 20 is preferred to minimize weight and optimize strength. In a preferred construction, apertures 160, 162, 164 and 166 are formed to reduce the material used in generally forming bracket assembly 20.

In a preferred construction, bracket assembly 20 is made from material that is light weight and provides minimal torque movement. Materials may be but are not limited to composites, plastic, laminated material, aluminum, or titanium. It is understood that alterations to the shown design of the bracket assembly 20 may be contemplated to provide other configurations for optimal strength and minimal weight.

Washer (not depicted) may be used between the outer cylinder 60 and bracket assembly 20 to generally decrease friction. Washer may be recessed into the brackets and/or outer cylinder to allow more precision fit of components against each other.

Joint Assembly Placement

Again referring to the drawings and in particular FIGS. 11, 11A, and 11B, in a preferred construction, the placement of the joint assembly 16 will be such that center axis 64 of rotation will generally fall through an anatomical weight line region 168. It is understood that typically according to the anatomical chart, weight line region 168 is approximately 28.2% of the foot length anterior to the posterior aspect of the skeletal structure of the foot. It is contemplated that joint assembly 16 rotation along center axis 64 rotation is generally along an anatomical center of rotation 170 of a natural ankle joint. It is understood that this position is in relatively close proximity to the posterior aspect of the foot, and as such the bracket assembly 20 for joint assembly 16 may begin just posterior to the weight line region 168 and run forward for support. It is further contemplated that positioning of the joint assembly 16 will provide additional keel 12 heel portion 26 compression abilities and uneven ground accommodation.

It should also be noted that while the keel 12 heel portion 26 will provide some compressibility from heel strike to foot flat, the majority of the action will come about through true plantarflexion of the keel 12 through the magnetorheological dampening in order to better mimic NHL and provide for optimal push off characteristics at toe off, which is discussed below.

Furthermore, an inversion/eversion damper system (not depicted) may be utilized at the base of the dampening system 18 to further accommodate uneven ground. This may include bumper systems, compressible materials such as urethane, joint systems, and the like.

Feed Back Sensor System

Referring to the drawings again and in particular FIG. 12, in a preferred embodiment, invention 10 may utilize a feed back sensor system 22. It is contemplated that feed back sensor system 22 will provide the dampening system 18 either directly or indirectly information such as but not limited to weight distribution on keel 12, forces generated on keel 12, impact times on portion of keel 12 and so forth for determination of user gait cycle to automatically control joint assembly 16 operations. Sensor system 22 may also include a strain sensor, moment sensor, pressure sensor, or the like that may communicate with microprocessor unit 172 via wires 186 as well as power source 130. Furthermore, feed back control system 22 may include a time sensor or real time clock and angle sensor to compare angular velocity and acceleration relative to center axis 64 of dampening system 18.

It is contemplated that invention 10 may further but not necessarily include a microprocessor unit 172 which communicates with sensor system 22 and in turn generally controls or communicates with the dampening system 18 of joint assembly 16 which will be discussed in greater detail below. It is understood that the term, feed back sensor system, should not be considered limiting.

It is contemplated feed back sensor system 22 may be generally located on keel 12. It is still further contemplated that feed back sensor system 22 may include heel sensor system 174 generally located on heel portion 26 and toe sensor system 176 generally located on toe portion 34.

Furthermore mechanical or liquid pressure/force strain sensors may be included within or part of dampening system 18 to determine force generally on heel portion 26 and/or toe portion 34. It is understood that other types of known sensors in the prior art may be used such as sensors that measures microscopic bending of the titanium tubular pylon to determine pressure on heel and forefoot.

In a preferred construction, heel sensor system 174 may further include sensor 178 and 180, on heal portion 26 medial segment 30 and likewise on heal portion 26 lateral segment 32 respectively. Furthermore, toe sensor system 176 may further include sensor 182 and 184 on toe portion 34 medial segment 38 and likewise on toe portion 34 lateral segment 40, respectively. It is contemplated that more sensors may be utilized and located around other portions of keel 12. In a preferred construction sensors and sensor systems communicate with dampening system 18 and/or microprocessor 172 via wires 186.

Microprocessor

It is contemplated that microprocessor unit 172 will give real time gait analysis throughout the gait cycle as well as control the MR fluid 94 liquidity, solidification, or viscosity. It is contemplated that microprocessor unit 172 may be of a similar design to that of the OTTO BOCKC-LEG, but should not be considered limited to such. This design may incorporate time sensors or real time clock 188, angular sensor 190, heel portion 26 load, force, strain, or moment sensor or sensors 192, and toe portion 34 load, force, strain, or moment sensor or sensors 194. It is also contemplated that moment sensors or strain gauges may be utilized.

Time sensors or real time clock 188 may be utilized to regulate events such as allowing invention 10 to lose all plantarflexion resistance when the user is sitting, thus, allowing the foot to be at a natural angle which is discussed in greater detail below. Furthermore, time clock 188 could regulate aspects of gait based on a profile of optimal timing for the user. It is further contemplated that some of the discussed functions may not necessarily only be based on time factors, but may also be based on movement or time and movement input to microprocessor. In a preferred construction, angular sensor 190 may be incorporated into the inner cylinder 80 and/or outer cylinder 60 to determine the relative angle of the keel 12 to user lower extremity. Angle sensor 190 may be fixed in the joint assembly 16 to determine the degree of rotation between inner cylinder 80 and outer cylinder 60. It is further contemplated that a level device (not depicted) may be used to generally determine the keel 12 angle relative to ground.

It is still further contemplated that microprocessor unit 172 could be programmed to control speed and amount of plantarflexion at keel 12 heal portion 26 striking of the ground also referred to as heel strike. It is also contemplated to utilize existing prior art such as OTTO BOCK C-LEG for control mechanisms. Furthermore, it is contemplated dynamic factors could be programmed to denote how "hard" a patient generally walks. The general amount of plantarflexion used in walking may be set to determine push off characteristics. For example, the speed and amount of dorsiflexion of the foot after toe off may be set. Each of these characteristics may be set for normal walking as well as adapt to change as the user gait changes. The sensory feedback systems 22 may cause the microprocessor unit 172 to change the MR fluid 94 damper characteristics as speed increases or decreases, or when walking on non-level terrain. Each aspect of ankle and foot gait characteristics may be modified through in order to appropriately tailor the user's gait for perfect symmetry, safety, and function of all activities. In a preferred embodiment, microprocessor unit 172 may be programmed with various memories or programs 196, include communication electronics 198 for interfacing or programming, and provide audible signals 200 or vibratory signals for warnings of malfunction, power level, etc. Microprocessor unit 172 could be located just anterior to the ankle joint assembly 16 on top of keel 12 or may be located on the inside of the inner cylinder 80, as generally discussed above. It is further contemplated that microprocessor unit 172 may be located on a lower extremity prosthesis wherein a user is missing possibly above knee or below knee but above ankle. In another preferred embodiment, invention 10 may work in conjunction with an artificial knee wherein microprocessor unit 172 could be utilized for both joint functions.

As generally discussed above, power source 130 is contemplated for electric supply for dampening system 18. It is further contemplated that power source 130 may be located in or integrally formed with microprocessor unit 172 and provide power for microprocessor unit 172. In a preferred construction, wires 173 may connect microprocessor 172 to power source 130. It is still further contemplated that microprocessor unit 172 may include a current supply and power or battery management system 202 for further optimizing power consumption. System 202 may include on and off timers for powering down while the invention is at rest for periods of time. Typically, unless the user is sleeping, there will be some change in angle or force at any given time frame when the user is supporting weight. It is contemplated that invention 10 may include an automatic system (not depicted) such that if no force change is detected on sensor system 22, during a designated time, invention 10 may power down to conserve energy. In a preferred embodiment, invention 10 would power down automatically when not being worn by the user whereby the user would not have to manually turn invention 10 off.

It is also still further contemplated that power source 130 may be of a regenerating nature wherein the power source 130 is re-supplied through mechanical means such as Faraday type device. Furthermore, known technology for self winding mechanisms with rotors, as found in self winding or self powering watches may be utilized. In a preferred embodiment, microprocessor unit 172 may be wirelessly programmed or controlled such as through wireless technology found in modern pacemakers/defibrillators. It is contemplated that a user could wirelessly regulate, command, or program specific functional parameters on demand such as modifying the dampening system 18 incrementally and selectively through a remote control. Likewise, invention 10 may include a hardwired controller (not shown) generally mounted in a relatively accessible manner on the invention 10.

As will be discussed in greater detail immediately below, microprocessor 172 may be used in conjunction with a myoelectric sensor system 400 and/or a proprioception system 300. In a preferred construction, microprocessor 172 may be utilized as the primary and only electronic control and processing device for invention 10. It is understood, however, that multiple units may be used that work in conjunction or separately to perform the various tasks.

Proprioception Stimulator

Referring again to the drawings and in particular FIG. 12A, in a preferred construction of invention 10, prosthetic proprioception system 300 may be included. It is contemplated that the invention 10 may provide instantaneous communication or signals from the prosthesis to the user wherein feedback is provided such that a sense of spatial and angular orientation of a prosthetic joint is achieved.

For reference, FIG. 12C generally illustrates elements of a natural human system for proprioception feedback pathway. Furthermore, FIG. 12D general illustrates a flow chart depicting elements of a natural human system for proprioception feedback.

It is understood that in the human body, the brain analyzes the required movements of our extremities as well as has knowledge of the positioning of our joints and orientation in space. Small proprioceptor sensors in the human muscles and joints, such as joint kinesthetic receptors, neuromuscular spindles, and neurotendinous receptors, send sensory information to the brain to tell it where the limb is orientated in space as well as its movements such as stretching of the muscles or bending of the joints.

It is also understood that there are systems in the prior art which relate to pressure sensor on the prosthetic foot or hand which may relay information through a small microprocessor and then stimulate the limb in a similar fashion, thus tricking the brain in thinking that the wearer is "feeling" with the prosthetic limb. It is contemplated that invention 10 may read the angular position and change within the prosthetic joint and stimulate the limb 308 in a designated manner, thus providing what may become a subconscious feedback of the position and angle of the limb's spatial orientation.

It is contemplated that invention 10 may provide greater safety through "knowing" the position of the prosthetic joint in space. By example, "knowing" or "feeling" that the ankle joint is plantar flexing excessively due to wearer beginning to walk down a hill.

Furthermore, it is also contemplated that there will be a decreased energy expenditure through providing a more natural gait pattern as well as providing an enhanced mental confidence in the prosthesis and therefore greater functionality. Likewise, the user may have a sense that the prosthesis is more of a part of them through enhanced human/machine interaction.

It is contemplated that the user's brain will learn the sensory feedback from the system as subconscious proprioception or cerebral projections.

It is contemplated that the user would generally connect, communicate, interact with joint assembly 16 via communication means or system 302. It is further contemplated that a separate microprocessor 304 may be utilized or microprocessor 172 or even a combination thereof. It is further understood that prosthetic proprioception system 300 may be utilized on other joints as well as ankle joints or other prosthetic joints, such as knee, hip, hand, elbow, and shoulder.

Furthermore, it is contemplated that the prosthetic proprioception system 300 may be utilized on an individual that has lost feeling or lost the sense of proprioception or control in their natural extremity.

In a preferred construction, it is contemplated that feedback mechanisms 306 may include pressure variance with angular change, pressure movement with angular change, electrical impulse to limb 308 with angular change, vibratory variance with angular change, and other conventionally known methods. Furthermore, it is contemplated that prosthetic proprioception system 300 may utilize angle or positional sensor in conjunction or separately with a sensor to detect resistance to angular change of a prosthetic joint.

Now referring to FIG. 12E, generally illustrated is a flow chart depicting a preferred embodiment of invention 10. It is contemplated that integration of the various sensors and feedback may be controlled by microprocessor 172 or through an independent processing system or combination thereof.

Referring now to FIG. 12F another preferred construction is generally depicted wherein keel 12, dampening system 18, ankle joint assembly 16, sensor system 22 is in general communication with wires 310 through microprocessor 312, power source 314, sensory stimuli contact 316 and wires 318. It is understood that microprocessor 312 may be microprocessor 172 or through an independent processing system or combination thereof. Power source 130 may also be used. Sensor system 22 may include angle or position sensor 320. Likewise, FIG. 12G is a general flow chart of a preferred embodiment invention 10 as discussed.

Now referring to FIG. 12H, another preferred embodiment of invention 10 is generally depicted wherein the prosthetic is directed to a non-ankle joint although a prosthetic hand is generally illustrated, it is understood that invention 10 may be utilized on other joints, prosthesis, and combination thereof. Socket 322, frame 324, sensory stimuli contact 326, wires 328, cosmetic cover hand shell 330, internal hand components 332, hand motor 334, hand connector piece 336, power source 338, microprocessor 340, angle/position sensor 342, and hand connection piece 344 are generally shown working in communication. Likewise it is understood that power source 338 may be utilized separately or in conjunction with power source 130 and may also be but is not limited to a myoelectric battery. It is also understood that microprocessor 340 may be microprocessor 172 or through an independent processing system or combination thereof.

Myoelectric Sensor System

Once again referring to the drawings and in particular FIG. 12B, a preferred construction of invention 10 may further include a myoelectric sensor system 400 wherein a generally closed loop sensory feedback system is contemplated. Myoelectric controls and/or myoelectric sensor system 400 may provide a prosthetic system wherein instantaneous communication or signals from the user to the prosthesis is achieved for better regulating, controlling, or positioning the prosthesis. It is understood that the human body produces electrical signal through muscular and other activity.

It is contemplated that in a preferred construction, dampening system 18 is generally controlled by the myoelectric sensor system 400. It is understood that myoelectric sensor system 400 may not necessarily cause movement of the ankle joint assembly 16, but rather is allowing the user to adjust the rotation or slow down the angle progression during stance. The joint assembly 16 movement may still generally be achieved through natural biomechanical movement during ambulation. The dampening system 18, corresponding sensor system 22 such as pressure, and myoelectric sensors system 400 generally limit how fast the ankle joint assembly 16 rotates. It is contemplated, therefore, anatomical musculature control of the lower extremity prosthesis, or more specifically the ankle joint assembly 16, is achieved.

It is further understood that myoelectric sensor system 400 may be utilized on other joints as well as ankle joints or other prosthetic joints, such as knee, hip, hand, elbow, and shoulder. Likewise, it is understood that myoelectric sensor system 400 and proprioception system 300 may be both included in a preferred embodiment or separately. It is understood that some myoelectric systems are known for use in upper extremity prosthetics and knee systems.

Myoelectric sensor system 400 may include stimulators or controls 402 which may be placed on the residual limb 404 of a user (i.e., on the pretibial and gastrocnemious group for transtibial amputees) to control or manage dampening system 18. By example, as the user fires their gastrocnemious muscle group, such as they naturally would during the midstance to toe off portion of the gait cycle at the beginning of midstance, invention 10 may increase resistance in the dampening system 18 and therefore provides greater resistance toward toe off portion of the gait cycle. User may then actively control their joint angle during ambulation as with a real foot.

It is contemplated that a preferred construction may enhance muscle tone and muscle strength in residual limb 404 and consequently may improve circulation. Of note, 70% of amputations are secondary to circulatory insufficiencies. Invention 10 may therefore prevent higher level amputations as is often the case with patients with severe circulatory insufficiencies.

Accordingly, invention 10 may also provide control for the user, increases safety, symmetry, confidence during ambulation, and further controls plantar-flexion and dorsi-flexion. Likewise, it is contemplated energy or power required myoelectric sensor system 400 and/or proprioception system 300 would be minimal relative to other power generally contemplated by invention 10.

Functions/Ambulation

Generally referring to the drawings and in particular FIGS. 13, 14, 14A, and 14B, the following changes to the invention 10 in general or dampening system 18 in specific may be allowed to best mimic natural human locomotion during ambulation.

Toe Off

Generally referring to FIG. 13, as the user completes the toe off position 204 of the gait cycle, the dorsiflexion spring system 137 may cause invention 10 to immediately begin to go into dorsiflexion, as occurs in normal human locomotion, to decrease the likelihood of stubbing the toe portion 34 during swing phase of gait. Once full dorsiflexion occurs, MR fluid 94 resistance of dampening system 18 remains at or near zero until heel strike position 206 when heel sensor system 174 detect pressure or load greater than zero. The rate of dorsiflexion can be programmed to allow for optimal safety and symmetry.

The spring load resistance of dorsiflexion spring system 137, may be modified or changed through adjusting the spring drive length, changing to a lighter or heavier spring, and/or through increasing dampening system 18 resistance, in order to optimize this characteristic for the user's activities. By example, if the user intends to run, the dorsiflexion spring system 137 resistance characteristics may be increased to overcome the inertial effects of the invention 10 during running.

Swing Phase

Throughout swing phase, invention 10 may remain in dorsiflexion until heel strike position 206 in order to generally shorten the extremity.

Heel Strike to Foot Flat

Heel strike position 206 cushioning and invention 10 plantarflexion comes about mainly though true ankle plantarflexion and not through heel compression. While the heel portion 26 may compress slightly, the ankle joint assembly 16 plantarflexion will constantly be monitored to provide fluid, smooth, roll-over characteristics and provide optimal push off characteristics through keel 12 loading. As heel portion 26 load, moment sensor 192, or heel sensor system 174 detect contact, foot plantarflexes with angle/time angular velocity using MR fluid 94 plantarflexor resistance. As the force of heel portion 26 contact increases, the MR fluid 94 resistance will increase to limit the force of plantarflexion.

It is contemplated that this will generally simulate the tibialis anterior action in human biomechanics at heel strike position 206. Once the toe portion 34 load sensor 194 or toe sensor system 176 is greater than or near zero at foot flat position 208, the angle sensor 190 or sensor system 22 in general may predict angular change per time for heel portion 26 strike pressure sensor or heel sensor system 174. If angle/time is too slow, according to heel portion 26 strike pressure or heel sensor system 174, MR fluid 94 resistance decreases. This would generally correspond to the slowing down of gait speed. If angular change increases with respect to previous step (going down a hill for instance), MR fluid 94 damper keeps plantarflexing until toe portion 34 load sensor or sensor system 176 is greater than zero.

It is contemplated that invention 10 will generally adapt to the surrounding environment automatically, in order to maintain proper stability, safety, and function. A similar effect would occur if the user were wearing a high-heeled shoe. It should be noted that at heel strike position 206 with many other prosthetic feet designs, the plantarflexion movement is obtained through heel compression. In a preferred construction, invention 10 does allow slight compression for shock absorption and smoothness of gait, but just as occurs biomechanically, the plantarflexion movement occurs through the ankle joint assembly 16 bending with an eccentric contraction of the tibialis anterior and not necessarily entirely through heel compression. It is contemplated that, the dampening system 18 allows for the controlled plantarflexion, mimicking the tibialis anterior movement, while the heel or heel portion 26 compression may mimic natural heel fatty pad compression for general shock absorption.

Foot Flat to Mid Stance

With increased heel sensor 174 pressure during heel strike position 206 to foot flat position 208, MR fluid 94 damper dorsiflexion resistance increases from foot flat position 208 to mid stance position 210 in order to provide increased plantarflexion during later portions of gait to allow increased spring off from invention 10 from heel off position 212 to toe off position 204. This may mimic the action of the gastrocnemious muscles during walking.

Mid Stance to Heel Off

With increased heel portion 26 sensor pressure or generally indication from heel sensor system 174 during heel strike position 206 to foot flat position 208, MR fluid 94 damper dorsiflexion resistance increases to provide increased plantarflexion during gait until toe portion 34 load sensor or toe sensor system 176 equals zero during toe off position 204. It is contemplated this may allow slight dorsiflexion to a certain angle for smoothness of gait but remains in some plantarflexion for push off from heel off position 212 to toe off position 204. During this section of gait, the MR fluid 94 dampening system 18 may lock out to provide the necessary plantarflexion for push off; however, the angle which the dampening system 18 of ankle joint assembly 16 will lock out will vary according to angular sensor 190, heel load sensor 192 during heel strike 206, and angular velocity determination, etc. During this portion of gait, the invention 10 goes into some dorsiflexion, however, the dorsiflexion is obtained in a preferred embodiment through keel 12 loading, therefore leading to increased push off at toe off position 204.

Heel Off to Toe Off

In natural human locomotion, the plantarflexor muscles fire at this stage in the gait cycle to maintain ankle angle or provide slight plantarflexion for push off. It is contemplated that through invention 10, the plantarflexion is already obtained through the midstance phase of gait and having the dampening system 18 lock out at a preferred or certain angle; however, it has been stored through keel 12 loading and is released in spring off from heel off position 212 to toe off position 204 thus simulating gastrocnemious induced plantarflexion of the foot. After heel portion 26 load sensor 192 equals zero and toe portion 34 pressure sensor nearly approaches zero, MR fluid 94 resistance goes to zero and allows for dorsiflexion spring system 137 to dorsiflex foot during swing phase.

Alterations from Normal Ambulation Function

A common complaint of many prosthetic foot users is that their prosthetic foot "sticks up" when they sit. This un-cosmetic appearance is eliminated through invention 10 by allowing the prosthetic to lose all plantarflexion resistance when the user is sitting, thus, allowing the foot to be at a natural angle. In a preferred construction, it should be noted that the dorsiflexion spring system 137 should not provide too much resistance to plantarflexing as to prevent the necessary motion in sitting, or to alter the gait pattern negatively. During sitting, it is contemplated that the dampening system 18 may prevent dorsiflexion while allowing plantarflexion to be free in order to provide greater cosmetic appearance. The sensor system 22 (time, angle, moment, etc) may determine if the user is sitting and will correspondingly allow invention 10 to plantarflex.

It is also contemplated that heel pressure, as generally determined by heel sensor system 174, that occurs for a given time period such as a few seconds, with no toe pressure, as generally indicated by toe sensor system 176, will indicate or allow plantarflexion for sitting wherein little to no resistance is created.

It is further contemplated that a negative bending moment on the heel portion 26 could signal the microprocessor unit 172 that the user has sat down and to have free plantarflexion abilities. A preferred embodiment may be by planting the heel portion 26 into the ground after sitting and pulling back. This action would generally not occur in normal walking and may therefore be a good indicator for sitting action.

In a preferred construction, invention 10 is constantly updating the sensory feedback system 22 information to the microprocessor unit 172 wherein the user can change heel heights of a shoe without changing any settings. If the user goes to a higher heel height for instance, the sensors system 22 will still read the moment forces and consider that the user is merely walking down a hill and, thus, the gait will not alter. The dampening system 18 can further be designed to allow a certain amount of heel height clearance accommodation. It is contemplated to allow about 15 degrees of dorsiflexion and about 45 degrees of plantarflexion to allow proper natural human locomotion and to allow for heel height changes. It is further contemplated that more or less degrees of rotation may be desired to allow for more or less of a range of motion to achieve natural human locomotion. It is understood that natural human locomotion may be altered or generally defined by such things as a users desire or need to wear high-heeled shoes.

In a preferred embodiment, invention 10 may have special modes to allow the user to lock the keel 12 or joint assembly 16 out at a given angle, such as for skiing, or can change the characteristics for other specific activities where limited motion is required. It is understood that various methods of implementing such is contemplated.

Stumbling or Walking Up Steep Hill

If toe load sensor 194 is greater than zero before heel load sensor 192 is greater than zero, then MR fluid 94 resistance will remain at or near zero or may fully lock up to stabilize joint assembly 16 if not fully dorsiflexed already, to continue to allow for full dorsiflexion via dorsiflexion spring system 137. In walking up a hill, this movement would still be similar to natural human locomotion and may benefit the user by decreasing or reducing hyperextension of the knee, as is found in the prior art.

Walking Down Hill

As angular sensor 190 determines that there is a greater angular change since heel strike position 206 and foot flat position 208, wherein toe load sensor 194 maybe greater than zero, invention 10 may provide slightly less dorsiflexion resistance from heel off position 212 to toe off position 204 to allow the user to descend down hill according to proper natural human locomotion.

Going Up Stairs

It is understood that generally a foot will already be in dorsiflexion after previous step and will remain in dorsiflexion as the stairs are ascended. Of note, typically invention 10 may not actually provide active push off during ambulation, but rather, on each step, providing the optimal keel 12 angle to enhance push off characteristics during gait. Thus, invention 10 generally allows for the greatest anterior support and energy return per walking speed and environment.

In going up stairs, biomechanically, active push off is achieved with gastrocnemious muscle activity. It is contemplated that invention 10 may be modified within the scope of the claims and description such that a generally heavier design with increased power output consumption may generally simulate the natural muscle activity in this action. It is further understood that in ascending stairs, the foot naturally goes into dorsiflexion for the first half of the ascent. A separate setting may also be included or programmed whereas the user may place the invention 10 in "stair ascent" mode to allow slight plantarflexion or, if preferred, less dorsiflexion.

Going Down Stairs

It is contemplated that if heel sensor 174 load or strike sensor 192 is greater than zero two steps or times in a row and no toe sensor 176 load or strike is observed, resistance in MR fluid 94 may increase at foot flat position 208 angle to prevent full plantarflexion and slipping off step. Still furthermore, as with the other ambulations generally described above, microprocessor unit 172 may be calibrated specifically for a user after a test run, sample, or base line is established of user performing the ambulation in an optimal manner. It is contemplated that by allowing the foot to plantarflex, invention 10 may improve ambulation in descending stairs.

Other Preferred Embodiments

Additionally, it is contemplated that invention 10 may be used in conjunction with myoelectric muscle contacts on the residual limb 404 for trans-tibial amputees and may provide greater control in ambulation. By example, at heel strike, tibialis anterior contraction may be used to determine the level of damper resistance of MR fluid 94 preventing or reducing too fast or too much plantarflexion. Also increased gastrocnemeous contraction during midstance may initiate dorsiflexion resistance sooner to allow keel 12 to remain in increased plantarflexion from midstance to toe off, therefore increasing push off may be utilized in fast walking or running.

Furthermore, invention 10 maybe used in conjunction with an orthotic device for a user who has lost the ability to actively plantarflex and/or dorsiflex their natural foot. It is contemplated that invention 10 dampening system 18, sensor system 22, microprocessor unit 172 and/or other elements or combinations thereof device may be located on the medial and/or lateral side of an orthotic brace and would control plantarflexion and dorsiflexion in a similar manner as is described above. Still furthermore, dampening system 18 may be used prosthetically or orthotically to control and manage other joints such as knee, hip, elbow, and the like.

Still furthermore, it is contemplated to provide an energy return adjustable heel height prosthetic foot. In a preferred embodiment, a manual lock would control the dampening system 18 by use of a permanent magnet placed against MR fluid 94 via a switch to adjust heel height. It is contemplated that this embodiment would not necessarily require sensory feedback system 22 or microprocessor unit 172 but would use the dampening system 18 to manually lock the ankle joint assembly 16 at a given angle to provide a user adjustable varied heel height foot.

Furthermore, the dampening system 18 may be altered to be an ankle unit only, with no keel, in order to be attached to other keel designs, or prosthetic feet in general.

Accordingly, other implementations are within the scope of the following claims. Changes may be made in the combinations, operations, and arrangements of the various parts and elements described herein without departing from the spirit and scope of the invention.

I claim:

1. A prosthetic ankle joint system for a user comprising:
a housing having an interior cavity, a center axis in said interior cavity, and an attachment means for fixedly connecting said housing to said user;
an inner cylinder disposed in said housing interior cavity wherein said inner cylinder rotates around said center axis of said housing;
a keel attached to said inner cylinder;
a sensor system located in said interior cavity of said housing having an angle sensor for determining said inner cylinder rotation amount respective to said housing; and
a dampening system in communication with said sensor system, said inner cylinder, and said housing for controlling dampening of the rotation of said inner cylinder around said center axis of said housing, comprising:
a microprocessor for processing said communication between said sensor system, said inner cylinder, said housing and wherein said dampening of the rotation is programably adjustable;
MR fluid in communication with said housing, said inner cylinder, and said microprocessor for electronically controlling said dampening of rotation;
a power source for operating said microprocessor; and
a sensory stimulus contact for attachment to said user and communicates with said microprocessor and generates proprioception sensory feedback to said user.

2. A prosthetic ankle joint system of claim 1 wherein said sensor system further includes a heel load sensor.

3. A prosthetic ankle joint system of claim 1 wherein said sensor system further includes a toe load sensor.

4. The prosthetic joint system of claim 1 further including more than one of said sensor stimulus contact.

* * * * *